United States Patent
Yifat et al.

(10) Patent No.: US 12,161,491 B2
(45) Date of Patent: Dec. 10, 2024

(54) DEPLOYABLE RADIATION SHIELD COVER

(71) Applicant: Radiaction Ltd., Tel Aviv (IL)

(72) Inventors: Jonathan Yifat, Ramat Hasharon (IL); Yossi Bar, Haifa (IL); Amir Belson, Savyon (IL)

(73) Assignee: Radiaction Ltd., Tel Aviv (IL)

( * ) Notice: Subject to any disclaimer, the term of this patent is extended or adjusted under 35 U.S.C. 154(b) by 320 days.

(21) Appl. No.: 17/567,430

(22) Filed: Jan. 3, 2022

(65) Prior Publication Data

US 2022/0117566 A1 Apr. 21, 2022

Related U.S. Application Data

(63) Continuation of application No. PCT/US2020/040365, filed on Jun. 30, 2020.

(60) Provisional application No. 62/869,675, filed on Jul. 2, 2019.

(51) Int. Cl.
*A61B 6/10* (2006.01)
*A61B 6/00* (2006.01)

(52) U.S. Cl.
CPC ............ *A61B 6/107* (2013.01); *A61B 6/4441* (2013.01); *A61B 6/4476* (2013.01)

(58) Field of Classification Search
CPC ..... A61B 6/107; A61B 6/4441; A61B 6/4476; A61B 2005/1094; A61B 2560/0285
USPC ................................. 250/515.1, 505.1, 519.1
See application file for complete search history.

(56) References Cited

U.S. PATENT DOCUMENTS

| | | | |
|---|---|---|---|
| 2,593,526 A | 4/1952 | Savage | |
| 2,835,824 A | 5/1958 | Schepker | |
| 3,310,053 A * | 3/1967 | Greenwood | A41C 1/00 |
| | | | 450/153 |
| 3,967,129 A | 6/1976 | Winkler | |
| 3,984,695 A | 10/1976 | Collica et al. | |
| 3,984,696 A | 10/1976 | Collica et al. | |
| 4,034,228 A | 7/1977 | Arauner | |
| 4,062,518 A | 12/1977 | Stivender et al. | |
| 4,122,350 A | 10/1978 | Lipthay et al. | |
| 4,140,129 A | 2/1979 | Heinz et al. | |

(Continued)

FOREIGN PATENT DOCUMENTS

| | | |
|---|---|---|
| CN | 1278713 A | 1/2001 |
| CN | 1331956 A | 1/2002 |

(Continued)

OTHER PUBLICATIONS

Yifat et al.; U.S. Appl. No. 18/181,532 entitled "Radiation protection apparatus and materials therefor," filed Mar. 9, 2023.

(Continued)

*Primary Examiner* — Jason L McCormack
(74) *Attorney, Agent, or Firm* — Shay Glenn LLP

(57) ABSTRACT

A radiation shield cover for covering a radiation shield of an X-ray system, the cover comprising cover sides; a cover bottom at the bottom of the cover sides configured to prevent contact of the radiation shield with a patient; a connection mechanism for connecting the cover to a radiation detector and/or a radiation source, and/or the radiation shield of the X-ray system; and a deployment mechanism configured to retract and/or extend the shield cover when the radiation shield retracts and/or extends, or thereafter.

20 Claims, 15 Drawing Sheets

(56) References Cited

U.S. PATENT DOCUMENTS

| | | |
|---|---|---|
| 4,210,811 A | 7/1980 | Dennhoven et al. |
| 4,400,820 A | 8/1983 | O'Dell et al. |
| 4,581,538 A | 4/1986 | Lenhart |
| 4,587,277 A | 5/1986 | Sato |
| 4,795,654 A | 1/1989 | Teleki |
| 4,837,796 A | 6/1989 | Ema |
| 4,938,233 A | 7/1990 | Orrison, Jr. |
| 4,969,170 A | 11/1990 | Kikuchi et al. |
| 4,977,585 A | 12/1990 | Boyd |
| 5,006,718 A | 4/1991 | Lenhart |
| 5,099,134 A | 3/1992 | Hase |
| 5,299,243 A | 3/1994 | Picco |
| 5,335,366 A | 8/1994 | Daniels |
| 5,417,225 A | 5/1995 | Rubenstein et al. |
| 5,438,705 A | 8/1995 | Mendez et al. |
| 5,523,578 A | 6/1996 | Herskovic |
| 5,525,408 A | 6/1996 | Weir et al. |
| 5,570,770 A | 11/1996 | Baaten et al. |
| 5,651,044 A | 7/1997 | Klotz, Jr. et al. |
| 5,769,816 A | 6/1998 | Barbut et al. |
| 5,769,819 A | 6/1998 | Schwab et al. |
| 5,848,449 A | 12/1998 | Hauger et al. |
| 5,900,638 A | 5/1999 | Jaeger et al. |
| 5,937,028 A | 8/1999 | Tybinkowski et al. |
| 5,947,981 A | 9/1999 | Cosman |
| 5,981,964 A | 11/1999 | Mcauley et al. |
| 6,003,174 A | 12/1999 | Kantrowitz et al. |
| 6,083,239 A | 7/2000 | Addis |
| 6,120,534 A | 9/2000 | Ruiz |
| 6,139,517 A | 10/2000 | Macoviak et al. |
| 6,245,012 B1 | 6/2001 | Kleshinski |
| 6,254,563 B1 | 7/2001 | Macoviak et al. |
| 6,254,633 B1 | 7/2001 | Pinchuk et al. |
| 6,258,120 B1 | 7/2001 | McKenzie et al. |
| 6,281,515 B1 | 8/2001 | Demeo et al. |
| 6,325,538 B1 | 12/2001 | Heesch |
| 6,352,363 B1 | 3/2002 | Munger et al. |
| 6,361,545 B1 | 3/2002 | Macoviak et al. |
| 6,371,935 B1 | 4/2002 | Macoviak et al. |
| 6,448,571 B1 | 9/2002 | Goldstein |
| 6,456,684 B1 | 9/2002 | Mun et al. |
| 6,459,091 B1 | 10/2002 | Demeo et al. |
| 6,481,888 B1 | 11/2002 | Morgan |
| 6,499,487 B1 | 12/2002 | McKenzie et al. |
| 6,537,297 B2 | 3/2003 | Tsugita et al. |
| 6,547,760 B1 | 4/2003 | Samson et al. |
| 6,636,757 B1 | 10/2003 | Jascob et al. |
| 6,653,648 B2 | 11/2003 | Goldstein |
| 6,674,087 B2 | 1/2004 | Cadwalader et al. |
| 6,692,513 B2 | 2/2004 | Streeter et al. |
| 6,703,632 B1 | 3/2004 | Macklis et al. |
| 6,709,415 B2 | 3/2004 | Navia et al. |
| 6,712,834 B2 | 3/2004 | Yassour et al. |
| 6,718,008 B1 | 4/2004 | He et al. |
| 6,828,578 B2 | 12/2004 | Demeo et al. |
| 6,841,791 B2 | 1/2005 | Demeo et al. |
| 7,029,175 B2 | 4/2006 | Karaus et al. |
| 7,044,958 B2 | 5/2006 | Douk et al. |
| 7,057,194 B2 | 6/2006 | Goldstein |
| 7,091,508 B2 | 8/2006 | Goldstein |
| 7,108,422 B2 | 9/2006 | Borom |
| 7,196,023 B2 | 3/2007 | Langley et al. |
| 7,232,453 B2 | 6/2007 | Shimon |
| 7,294,845 B2 | 11/2007 | Ballsieper |
| 7,331,712 B2 | 2/2008 | Fischer et al. |
| 7,391,042 B2 | 6/2008 | Goldstein |
| 7,420,193 B2 | 9/2008 | Treuth |
| 7,440,539 B2 | 10/2008 | Danielsson et al. |
| 7,441,954 B2 | 10/2008 | Bernhardt |
| 7,465,947 B2 | 12/2008 | Magram |
| 7,537,600 B2 | 5/2009 | Eskuri |
| 7,648,273 B2 | 1/2010 | Manzke et al. |
| 7,829,873 B2 | 11/2010 | Fox et al. |
| 7,837,385 B2 | 11/2010 | Klingenbeck-Regn |
| 7,897,949 B2 | 3/2011 | Ballsieper |
| 8,052,717 B2 | 11/2011 | Mujkanovic |
| 8,113,713 B2 | 2/2012 | Belson et al. |
| 8,114,114 B2 | 2/2012 | Belson |
| 8,123,779 B2 | 2/2012 | Demond et al. |
| 8,298,258 B2 | 10/2012 | Anderson et al. |
| 8,337,519 B2 | 12/2012 | Wasicek |
| 8,382,788 B2 | 2/2013 | Galdonik et al. |
| 8,420,902 B2 | 4/2013 | Gilsinger |
| 8,439,564 B2 | 5/2013 | Belson et al. |
| 8,460,777 B2 | 6/2013 | Long |
| 8,639,564 B2 | 1/2014 | Toebes et al. |
| 8,740,930 B2 | 6/2014 | Goodwin |
| 8,903,038 B2 | 12/2014 | Matsuzawa et al. |
| 8,968,354 B2 | 3/2015 | Wang et al. |
| 9,144,485 B2 | 9/2015 | Bergheim |
| 9,370,331 B2 | 6/2016 | Belson et al. |
| 9,492,265 B2 | 11/2016 | Russell et al. |
| 9,744,023 B2 | 8/2017 | Wang et al. |
| 9,877,821 B2 | 1/2018 | Russell et al. |
| 9,907,519 B2 | 3/2018 | Belson et al. |
| 10,244,996 B2 | 4/2019 | Belson et al. |
| 10,617,509 B2 | 4/2020 | Kleshinski et al. |
| 10,709,395 B2 | 7/2020 | Stegehuis et al. |
| 11,076,819 B2 | 8/2021 | Belson et al. |
| 11,152,128 B2 | 10/2021 | Yifat et al. |
| 11,179,287 B1 | 11/2021 | Mirbahaeddin |
| 11,399,927 B2 | 8/2022 | Kleshinski et al. |
| 11,547,375 B2 | 1/2023 | Yifat et al. |
| 11,621,096 B2 | 4/2023 | Yifat et al. |
| 11,744,529 B2 | 9/2023 | Yifat et al. |
| 2002/0003854 A1 | 1/2002 | Ivan et al. |
| 2002/0015471 A1 | 2/2002 | Yagi |
| 2002/0048089 A1 | 4/2002 | Brown |
| 2002/0193686 A1 | 12/2002 | Gilboa |
| 2003/0084512 A1 | 5/2003 | Fujita et al. |
| 2003/0100940 A1 | 5/2003 | Yodfat |
| 2003/0112924 A1 | 6/2003 | Seufert |
| 2003/0174802 A1 | 9/2003 | Hare |
| 2004/0020829 A1 | 2/2004 | Magna et al. |
| 2004/0029998 A1 | 2/2004 | Tomita |
| 2004/0042587 A1 | 3/2004 | Deshpande |
| 2004/0208291 A1 | 10/2004 | Stout |
| 2004/0257744 A1 | 12/2004 | Bushko et al. |
| 2005/0010246 A1 | 1/2005 | Streeter et al. |
| 2005/0070779 A1 | 3/2005 | Singh et al. |
| 2005/0213713 A1 | 9/2005 | Cadwalader et al. |
| 2005/0236588 A1 | 10/2005 | Ein-Gal |
| 2005/0283186 A1 | 12/2005 | Berreda et al. |
| 2006/0097734 A1 | 5/2006 | Roziere |
| 2006/0251219 A1 | 11/2006 | Cadwalader et al. |
| 2006/0262898 A1 | 11/2006 | Partain et al. |
| 2006/0287668 A1 | 12/2006 | Fawzi et al. |
| 2007/0086570 A1 | 4/2007 | Spahn |
| 2007/0189442 A1 | 8/2007 | Sukovic et al. |
| 2007/0242805 A1 | 10/2007 | Somers |
| 2007/0269012 A1 | 11/2007 | Somers |
| 2008/0119722 A1 | 5/2008 | Swaney |
| 2008/0258929 A1 | 10/2008 | Maschke |
| 2008/0304626 A1 | 12/2008 | Camus |
| 2009/0010389 A1 | 1/2009 | Ma et al. |
| 2009/0088327 A1 | 4/2009 | Rigatti et al. |
| 2009/0232282 A1* | 9/2009 | Belson ................ A61B 6/4441 |
| | | 378/209 |
| 2009/0325172 A1 | 12/2009 | Milton et al. |
| 2010/0010535 A1 | 1/2010 | Mujkanovic |
| 2010/0028885 A1 | 2/2010 | Balasubramanian et al. |
| 2010/0061509 A1 | 3/2010 | D'Ambrosio et al. |
| 2010/0094119 A1 | 4/2010 | Yu et al. |
| 2010/0133450 A1 | 6/2010 | Belson et al. |
| 2010/0163758 A1* | 7/2010 | Kirschenbaum ......... G21F 3/02 |
| | | 250/516.1 |
| 2010/0312268 A1 | 12/2010 | Belson |
| 2011/0314594 A1 | 12/2011 | Rogers et al. |
| 2012/0271340 A1 | 10/2012 | Castellano et al. |
| 2013/0129449 A1 | 5/2013 | Ishikawa |
| 2013/0204113 A1 | 8/2013 | Carmi |
| 2013/0267993 A1 | 10/2013 | Carpenter |
| 2013/0270462 A1 | 10/2013 | Beck |
| 2014/0000091 A1 | 1/2014 | Angel et al. |

(56) References Cited

U.S. PATENT DOCUMENTS

| | | | |
|---|---|---|---|
| 2014/0029720 A1 | 1/2014 | Osherov et al. | |
| 2014/0033437 A1 | 2/2014 | Gross et al. | |
| 2014/0048730 A1 | 2/2014 | Niedzielski et al. | |
| 2014/0214069 A1 | 7/2014 | Franklin | |
| 2014/0249568 A1 | 9/2014 | Adams et al. | |
| 2014/0275998 A1 | 9/2014 | Eichler et al. | |
| 2014/0332701 A1* | 11/2014 | Byers | G21F 3/00 250/519.1 |
| 2014/0334608 A1 | 11/2014 | Mulzer et al. | |
| 2015/0006607 A1 | 1/2015 | E | |
| 2015/0117615 A1 | 4/2015 | Dirauf et al. | |
| 2015/0128727 A1 | 5/2015 | Sattler et al. | |
| 2015/0305694 A1 | 10/2015 | Sakata | |
| 2015/0359505 A1 | 12/2015 | Hoshino | |
| 2015/0366650 A1 | 12/2015 | Zi et al. | |
| 2016/0029980 A1 | 2/2016 | Osherov et al. | |
| 2016/0038365 A1 | 2/2016 | Conner et al. | |
| 2016/0143600 A1 | 5/2016 | Schmidt | |
| 2016/0150837 A1 | 6/2016 | Kaforey et al. | |
| 2016/0158082 A1 | 6/2016 | Gainor et al. | |
| 2016/0193731 A1 | 7/2016 | Sattler et al. | |
| 2016/0286890 A1 | 10/2016 | Morin et al. | |
| 2016/0317277 A1 | 11/2016 | Carpenter et al. | |
| 2016/0345929 A1 | 12/2016 | Azizian et al. | |
| 2017/0220709 A1 | 8/2017 | Wan et al. | |
| 2017/0265824 A1 | 9/2017 | Wasson et al. | |
| 2017/0278585 A1 | 9/2017 | Almer et al. | |
| 2017/0347978 A1 | 12/2017 | Kuspert | |
| 2018/0000431 A1 | 1/2018 | Roth et al. | |
| 2018/0029972 A1 | 2/2018 | Daly | |
| 2018/0168525 A1 | 6/2018 | Belson et al. | |
| 2018/0206970 A1 | 7/2018 | Eggert et al. | |
| 2018/0214100 A1 | 8/2018 | Kumar | |
| 2018/0227468 A1 | 8/2018 | Pritz | |
| 2018/0249972 A1 | 9/2018 | Yifat et al. | |
| 2018/0250183 A1 | 9/2018 | Zwierstra et al. | |
| 2018/0289342 A1 | 10/2018 | Chandwadkar et al. | |
| 2019/0015152 A1 | 1/2019 | Howard et al. | |
| 2019/0038377 A1 | 2/2019 | Wortmann et al. | |
| 2019/0059852 A1 | 2/2019 | Zwierstra et al. | |
| 2020/0205754 A1 | 7/2020 | Yifat et al. | |
| 2021/0283425 A1 | 9/2021 | Kim et al. | |
| 2022/0071576 A1 | 3/2022 | Foster et al. | |
| 2022/0110594 A1 | 4/2022 | Belson et al. | |
| 2023/0091397 A1 | 3/2023 | Kleshinski et al. | |
| 2023/0181132 A1 | 6/2023 | Yifat et al. | |

FOREIGN PATENT DOCUMENTS

| | | |
|---|---|---|
| CN | 1442117 A | 9/2003 |
| CN | 101164637 A | 4/2008 |
| CN | 201216602 Y | 4/2009 |
| CN | 202665566 U | 1/2013 |
| CN | 203303071 U | 11/2013 |
| CN | 203341747 U | 12/2013 |
| CN | 203898342 U | 10/2014 |
| CN | 103045983 B | 12/2015 |
| CN | 106413578 A | 2/2017 |
| CN | 205959627 U | 2/2017 |
| CN | 107224297 A | 10/2017 |
| CN | 204016322 U | 12/2017 |
| CN | 108309664 A | 7/2018 |
| CN | 207627457 U | 7/2018 |
| DE | 19924914 A1 | 12/2000 |
| DE | 102012212104 A1 | 1/2014 |
| DE | 102013214222 A1 | 1/2015 |
| DE | 102014215448 B3 | 12/2015 |
| EP | 0393214 A1 | 10/1990 |
| EP | 3481301 A1 | 5/2019 |
| FR | 2736256 A1 | 1/1997 |
| JP | H0739805 U | 7/1995 |
| JP | H06278082 | 10/1997 |
| JP | 2001037751 A | 2/2001 |
| JP | 2004506911 A | 3/2004 |
| JP | 2004264207 A | 9/2004 |
| JP | 2005003755 A | 1/2005 |
| JP | 2005177047 A | 7/2005 |
| JP | 2008079728 A | 4/2008 |
| JP | 2009232339 A | 10/2009 |
| JP | 2011511265 A | 4/2011 |
| JP | 2016107655 A | 6/2016 |
| JP | 2017181375 A | 10/2017 |
| JP | 6391149 B2 | 9/2018 |
| JP | 2019523040 A | 8/2019 |
| JP | 7132854 B2 | 9/2022 |
| JP | 2023158023 A | 10/2023 |
| KR | 20120084574 A | 7/2012 |
| KR | 101218378 B1 | 1/2013 |
| KR | 20150099969 A | 9/2015 |
| WO | WO96/01591 A1 | 1/1996 |
| WO | WO03/073939 A1 | 9/2003 |
| WO | WO2004/019817 A1 | 3/2004 |
| WO | WO2005/102174 A1 | 11/2005 |
| WO | WO2006/026646 A1 | 3/2006 |
| WO | WO2006/092078 A1 | 9/2006 |
| WO | WO2007/060561 A2 | 5/2007 |
| WO | WO2008/140486 A2 | 11/2008 |
| WO | WO2013/129449 A1 | 9/2013 |
| WO | WO-2017083437 A1 | 5/2017 |
| WO | WO2017/116828 A1 | 7/2017 |
| WO | WO2018/007437 A1 | 1/2018 |
| WO | WO-2018232037 A1 | 12/2018 |
| WO | WO2020/142556 A1 | 7/2020 |
| WO | WO-2020142560 A1 | 7/2020 |
| WO | WO-2020142564 A1 | 7/2020 |
| WO | WO-2021003191 A1 | 1/2021 |

OTHER PUBLICATIONS

Yifat et al.; U.S. Appl. No. 18/355,680 entitled "Supplementary collision detection and prevention system for a medical imager," filed Jul. 20, 2023.

International Search Report and Written Opinion of the International Searching Authority dated Sep. 30, 2020.

EP20835541.2 Extended European Search Report dated Jun. 19, 2023.

Yifat et al., U.S. Appl. No. 18/605,540 entitled "Radiation shielding apparatuses and applications thereof," filed Mar. 14, 2024.

Yifat et al.; U.S. Appl. No. 18/661,544 entitled "Patient head protection device," filed May 10, 2024.

* cited by examiner

DEPLOYABLE RADIATION SHIELD COVER

CROSS REFERENCE TO RELATED APPLICATIONS

This application is a continuation of PCT Application No. PCT/US20/40365, filed Jun. 30, 2020, which claims priority from U.S. Provisional Patent Application No. 62/869,675, filed Jul. 2, 2019, the disclosure of which is incorporated by reference herein in its entirety.

FIELD OF THE INVENTION

The present invention relates to radiation protection equipment, in particular a radiation shield cover for covering a radiation shield to prevent patient contamination.

BACKGROUND OF THE INVENTION

X-ray equipment is routinely used in various applications and systems. For example, in medical settings, X-ray is vastly used as a diagnostic tool. Nevertheless, healthcare providers, and technical personnel, who operate X-ray systems are usually exposed to radiation and may be harmed by such cumulative X-ray exposure.

X-ray shielding equipment, e.g., a fluoroscopy C-arm shield, can be advantageously used to reduce exposure of the medical team to stray radiation during X-ray procedures. Among the challenges associated with shielding equipment (e.g., a C-arm fluoroscopy shielding apparatus) is the requirement to maintain sterility and prevent cross-patient contamination.

Exemplary teachings in the field and art of the invention are provided in the following disclosures by the same applicant/assignee of the present invention: U.S. Pat. Nos. 8,439,564; 8,113,713; 9,370,331; 9,907,519; 10,244,996; US 2018/249,972; PCT/US2019/069158; and PCT/US2019/069162; the teachings of which are incorporated by reference as if fully set forth herein.

SUMMARY OF THE INVENTION

The present invention relates to a cover for a radiation shield or radiation blocking apparatus to ensure cleanliness. The invention particularly pertains to a cover that can expand (e.g. be extended) and retract (e.g., fold) providing a sterile barrier between radiation shielding equipment and/or an X-ray system or portions thereof and a patient.

The cover is configured to be place-able over at least a portion of a radiation shield to provide a sterile barrier between the radiation shield, and/or a C-arm detector and/or source, or the like, of X-ray imaging equipment and a patient, to prevent possible cross-patient contamination.

According to one aspect of the present invention there is provided a radiation shield cover for covering a radiation shield of an X-ray system, the cover comprising:
  a radiation shield cover sides;
  a cover bottom at the bottom of the cover sides configured to prevent contact of the radiation shield with a patient; and
  a connection mechanism for connecting the cover to a radiation detector and/or a radiation source, and/or the radiation shield of the X-ray system.

According to another aspect, the invention provides a radiation shield cover for covering a radiation shield of an X-ray system, the cover comprising:
  a. cover sides;
  b. a cover bottom at the bottom of the cover sides configured to prevent contact of the radiation shield with a patient;
  c. a connection mechanism for connecting the cover to a radiation detector and/or a radiation source, and/or the radiation shield of the X-ray system; and
  d. a deployment mechanism configured to retract and/or extend the shield cover when the radiation shield retracts and/or extends, or thereafter.

According to another aspect, the invention provides a radiation shield covering apparatus comprising:
  a. a deployment mechanism; and
  b. a radiation shield cover having cover sides, and a cover bottom at the bottom of the cover sides configured to prevent contact of the radiation shield with a patient,
  c. wherein the deployment mechanism is configured to retract and/or extend the radiation shield cover.

In one or more embodiments, the cover sides are configured to attach to the radiation detector and/or the radiation source and/or the radiation shield.

In one or more embodiments, the cover includes a connection mechanism for connecting thereof to the radiation detector and/or the radiation source and/or the X-ray radiation shield.

In one or more embodiments, the connection mechanism includes a cover top with an opening having a peripheral elastic band.

In one or more embodiments, the cover is designed to be disposable.

In one or more embodiments, the cover further includes a deployment mechanism associated therewith and configured to retract the radiation shield cover. In one or more embodiments, the cover further includes a deployment mechanism associated therewith and configured to extend the radiation shield cover. In one or more embodiments, the deployment mechanism is not configured to extend the radiation shield cover.

In one or more embodiments, the deployment mechanism includes a pump fluidly connected to at least one hydraulically operated telescopic device, which is operably connected to the cover.

In one or more embodiments, the deployment mechanism includes a motor and a cable operably connected to the motor and a telescopic device.

In one or more embodiments, the deployment mechanism includes at least one elastic member operably connected to the cover.

In one or more embodiments, the deployment mechanism includes at least one cover-to-shield fastener.

In one or more embodiments, the at least one cover-to-shield fastener includes an anchor, connected to the shield at the external side thereof; and a hook connected to an internal side of the cover.

In one or more embodiments, the deployment mechanism includes at least one shield cover cable; at least one inter-cable fastener; at least one motor-shaft cable; and at least one electric motor having a motor shaft, wherein the shield cover cable is connected at one end to a distal portion of the cover and at its other end to inter-cable fastener, and the motor-shaft cable is connected at one end to inter-cable fastener and at its other end to the motor shaft.

In one or more embodiments, the shield cover cable is attached to the cover and can be removed along with the shield cover.

In one or more embodiments, when the electric motor is operated and the motor shaft rotates, the motor-shaft cable is wound on the motor shaft or unwound from the shaft.

In one or more embodiments, during retraction of the cover, the motor-shaft cable is configured to wound on the motor shaft and wherein during extension, the motor-shaft cable is configured to unwind on the motor shaft In one or more embodiments, the at least one electric motor is connected to two motor-shaft cables disposed along a same face of the cover, where one of the shaft cables is attached at a lower portion or side of the motor shaft and the other motor-shaft cable is attached at an upper portion or side of the motor shaft, whereby when the electric motor is operated and motor shaft rotates, the two motor-shaft cables will simultaneously be wound on the motor shaft or simultaneously unwind from the shaft.

In one or more embodiments, the at least one electric motor is connected to a motor-shaft cable disposed along a same face of the cover, whereby when the electric motor is operated and motor shaft rotates, the motor-shaft cable will simultaneously be wound on the motor shaft or simultaneously unwind from the shaft.

In one or more embodiments, the at least one electric motor is connected to two motor-shaft cables disposed along a same face of the cover, where one of the shaft cables is attached at a lower portion or side of the motor shaft and the other motor-shaft cable is attached at an upper portion or side of the motor shaft, whereby when the electric motor is operated and motor shaft rotates, the two motor-shaft cables will simultaneously be wound on the motor shaft or simultaneously unwind from the shaft.

In one or more embodiments, the at least one electric motor includes oppositely extending motor shafts, each of the shafts having a shaft accessory with a shaft bearing disposed thereon, the shaft accessory having a larger diameter than the shafts, and being configured with a motor-shaft cable to simultaneously wind on one of the shafts during retraction of the cover and to unwind therefrom during extension of the cover.

In one or more embodiments, the motor-shaft cable and/or the shield cover cable includes a motor-stop sensor and a visual sensor stop flag, the motor-stop sensor configured to sense when the flag arrives in the retracting direction and to send a signal to the electric motor to stop operating and thereby prevent overwind.

In one or more embodiments, the deployment mechanism includes at least one pulley system configured to contract and expand to respectively release and pull the cables.

In one or more embodiments, the at least one pulley system includes a generally horizontal rod, which is raised and lowered by a linear motor.

In one or more embodiments, the deployment mechanism includes one or more vertical stabilizing rods to stabilize the generally horizontal rod.

In one or more embodiments, the horizontal rod, is stabilized by one or more vertical stabilizing rods upon which one or more stabilizing rings can slide.

In one or more embodiments, the deployment mechanism includes a shield cover cable attached to a corner of the cover and the shield cover cable runs through a sleeve.

In one or more embodiments, the deployment mechanism includes a shield cover cable attached to a corner of the cover and the shield cover cable runs through a series of rings.

In one or more embodiments, the deployment mechanism includes a shield cover cable with a series of cable-to-cover cables extending from a series of locations along the shield cover cable to a series of corresponding locations along an edge of the cover.

In one or more embodiments, the shield cover cable has a plurality of cable-to-cover cables extending from the distal end of the shield cover cable to locations including those at and adjacent a corner at the bottom and one of the sides of the cover.

In one or more embodiments, there are four cover sides forming a square-like profile. In one or more embodiments, there are three cover sides forming a triangular profile. In one or more embodiments, the cover has a round profile.

BRIEF DESCRIPTION OF THE DRAWINGS

The invention may be more clearly understood upon reading of the following detailed description of non-limiting exemplary embodiments thereof, with reference to the following drawings, in which.

Figure 1:
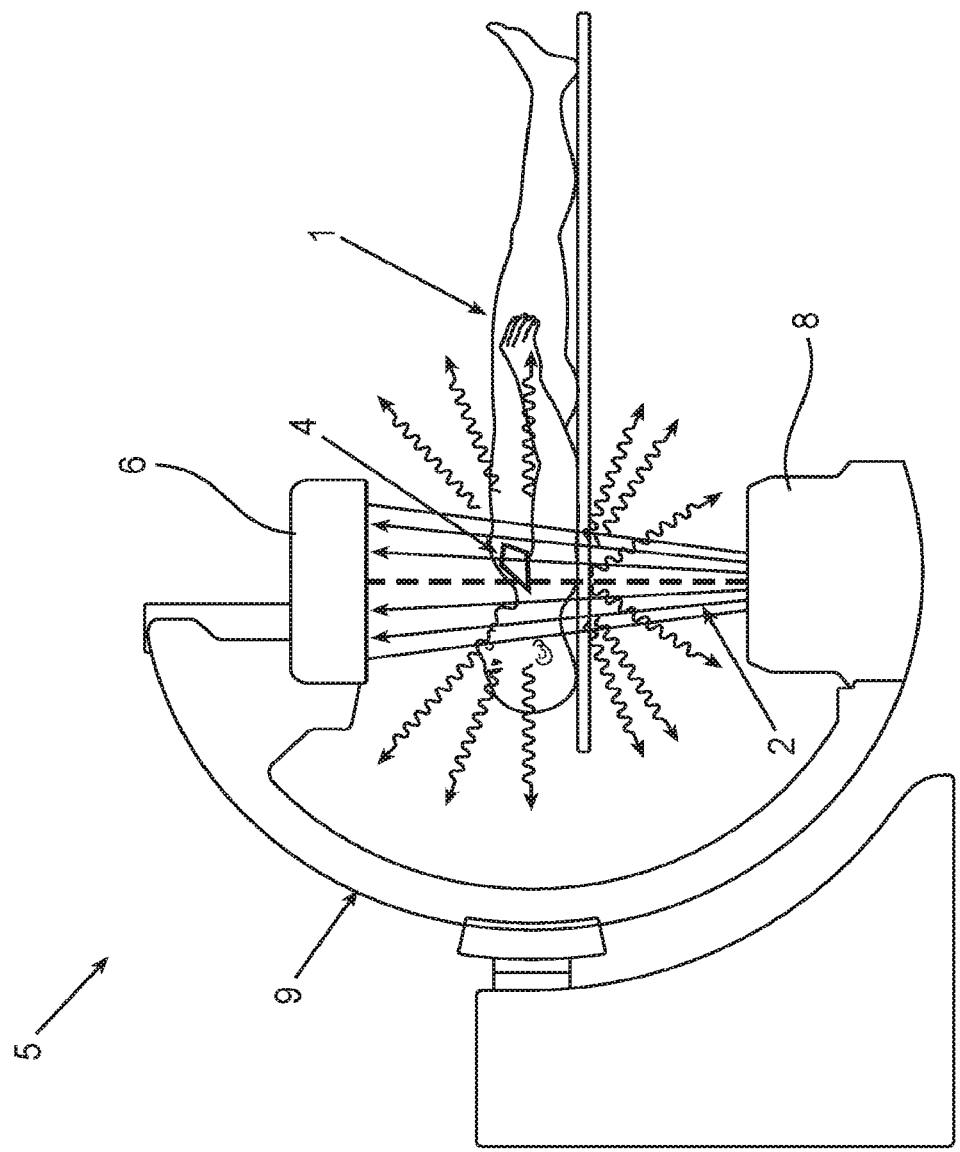
FIG. 1 is a side view of an exemplary prior art C-arm of an X-ray system.

The following detailed description of embodiments of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DETAILED DESCRIPTION OF EMBODIMENTS

Illustrative embodiments of the invention are described below. In the interest of clarity, not all features/components of an actual implementation are necessarily described.

Repeated exposure to X-ray radiation due to medical use of X-ray systems causes substantial harmful health effects. Consequently, radiation shielding apparatus configured for shielding (protecting) the surrounding from stray radiation of X-ray has been previously devised by at least some of the inventors of the present invention. Exemplary such radiation shielding apparatuses are provided in the following previously filed disclosures by the same applicant/assignee of the present invention: U.S. Pat. Nos. 8,439,564 and 8,113,713, and International Application No. WO/2017/083437, the teachings of which are herein incorporated by reference.

The present invention, in some embodiments thereof, pertains to covers of a radiation shielding apparatus, which can afford a sterile barrier between an X-ray system or portions thereof, and a patient and/or health care staff, to prevent possible cross-patient contaminations.

Possible advantages of some embodiments of the present invention include that the X-ray shield cover is simple, reliable, cost effective, easily attachable, replaceable and compact.

Advantageously, the cover is removable and can be disposable or reusable (i.e., can be sterilized with various known sterilization techniques). Optionally, the cover is disposable and accessories related thereto are reusable. Further optionally, the cover is disposable, and deployment mechanisms thereof are reusable. Further optionally, the cover along with deployment mechanism thereof is reusable.

Embodiments of the present invention may be used to provide an accessory or a supplementary product, which can be used along with a radiation shielding apparatus to allow sterile/cleaner surroundings to a patient during X-ray procedures. Further exemplary embodiments of the invention pertain to a C-arm radiation shielding apparatus and to deployable covers thereof.

The herein shield cover may be transparent, translucent or opaque. The cover may be made from various flexible, light weight and/or expandable materials. Non-limiting examples for the material of the cover include polyethylene and polyvinyl chloride.

The cover includes a deployment mechanism configured to retract the cover. Additionally, or alternatively, the deployment mechanism includes an extension mechanism allowing the cover to extend. Non-limiting examples of deployment mechanisms include, hydraulic pistons, telescopic members, springs, cables with a cable retraction-extension mechanism (e.g., a motorized roller mechanism) and the like.

The present radiation shield cover, may be described herein the specification and claims, in the singular, regardless that a pair of such covers may be used with respect to a C-arm X-ray system; for example, an upper cover may be attached/attachable to the detector of the C-arm, and a lower cover may be attached/attachable to the source of the C-arm.

The term 'X-ray system', and its derivatives, is used herein in a non-limiting manner, and refers to any radiography or radiotherapy X-ray emitting type system, such as digital radiology, fluoroscopy, angiography (C-arms) or digital X-ray systems. The term may also refer to X-ray emitting type systems suitable for use in non-medical applications.

Figure 2:
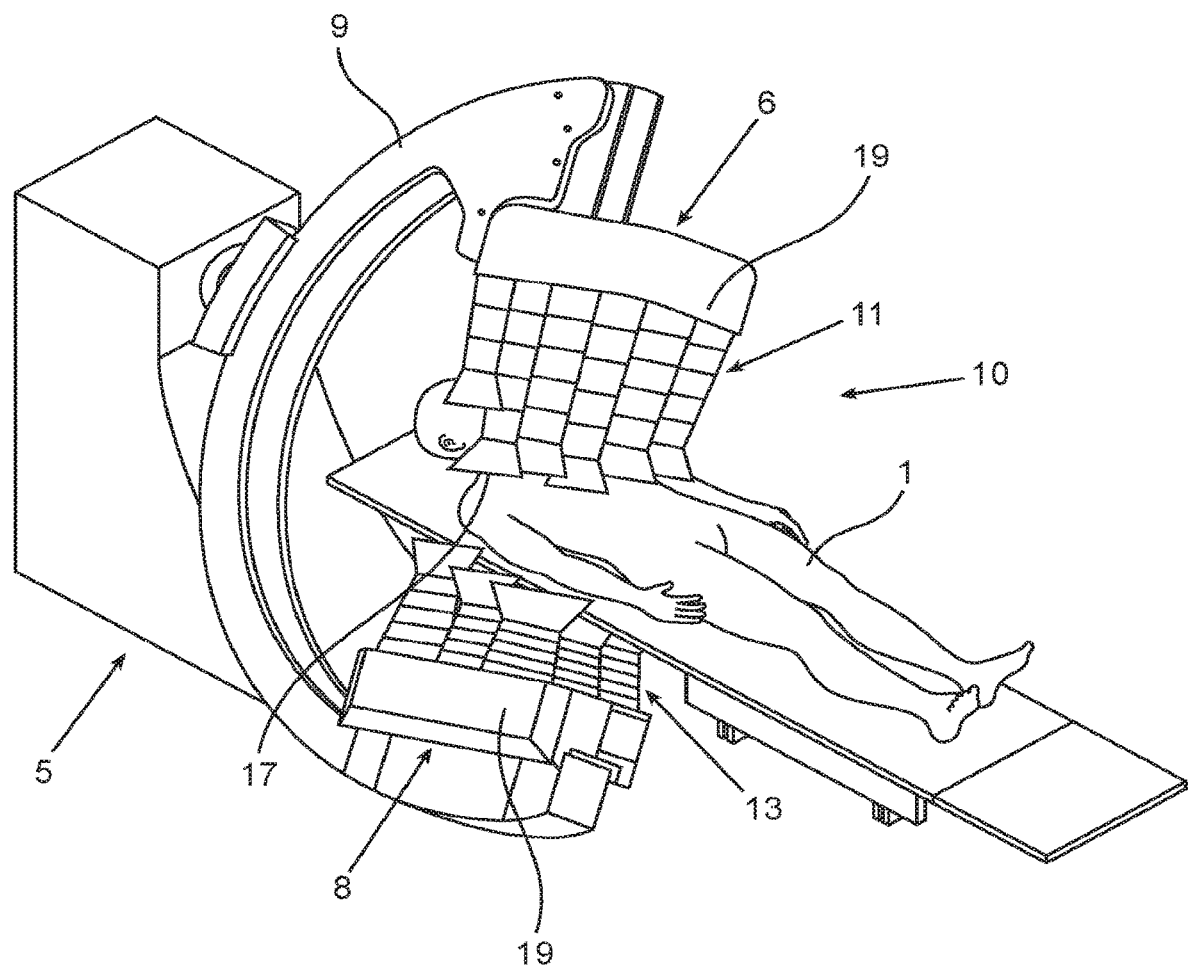
FIG. 2 is a perspective view of the C-arm of FIG. 1 with an exemplary prior art radiation shield connected thereto.

FIG. 1 illustrates an exemplary prior art C-arm X-ray system 5; and FIG. 2 illustrates an exemplary prior art radiation shielding apparatus 10, configured to protect the surroundings from scattered X-rays emitted by X-ray system 5. X-ray system 5 includes a radiation source 8 and a radiation detector 6 mounted on opposite ends of a C-arm 9. Radiation source 8 emits an X-ray beam 2 that passes through an imaged area 4 of a patient 1 toward radiation detector 6, which records the exposure to X-ray radiation and sends the image or video feed to a computer and/or display either in real time, or at a later time.

FIG. 2 shows an upper radiation shield 11 and a lower radiation shield 13, which include and are respectively peripherally coupled to radiation detector 6 and radiation source 8 of C-arm 9 via a support base 19. Radiation shields 11, 13 provide radiation shielding to the surroundings to protect X-ray technicians and staff. Shields 11, 13 have free ends or free edges 17, which may come in soft contact with the patient 1. Shields 11, 13 are further dynamically retractable and extendable via dedicated motorized retraction/extension mechanisms (not shown).

Figure 3A:
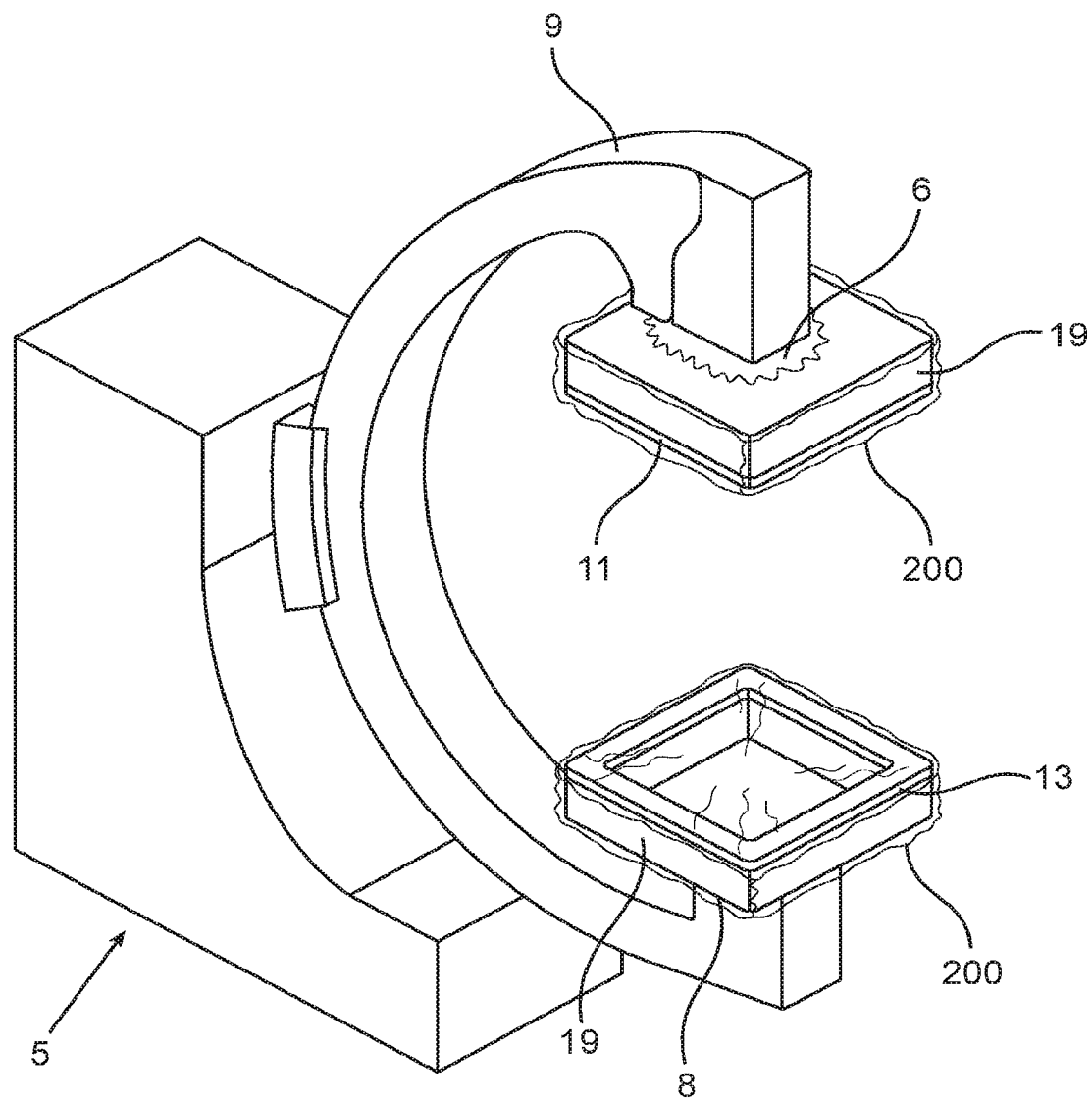
FIGS. 3A and 3B are perspective views of an exemplary deployable radiation shield cover, in accordance with embodiments of the present invention, in the retracted and extended positions, respectively, attached to the C-arm of FIG. 1 or 2.
Figure 3B:
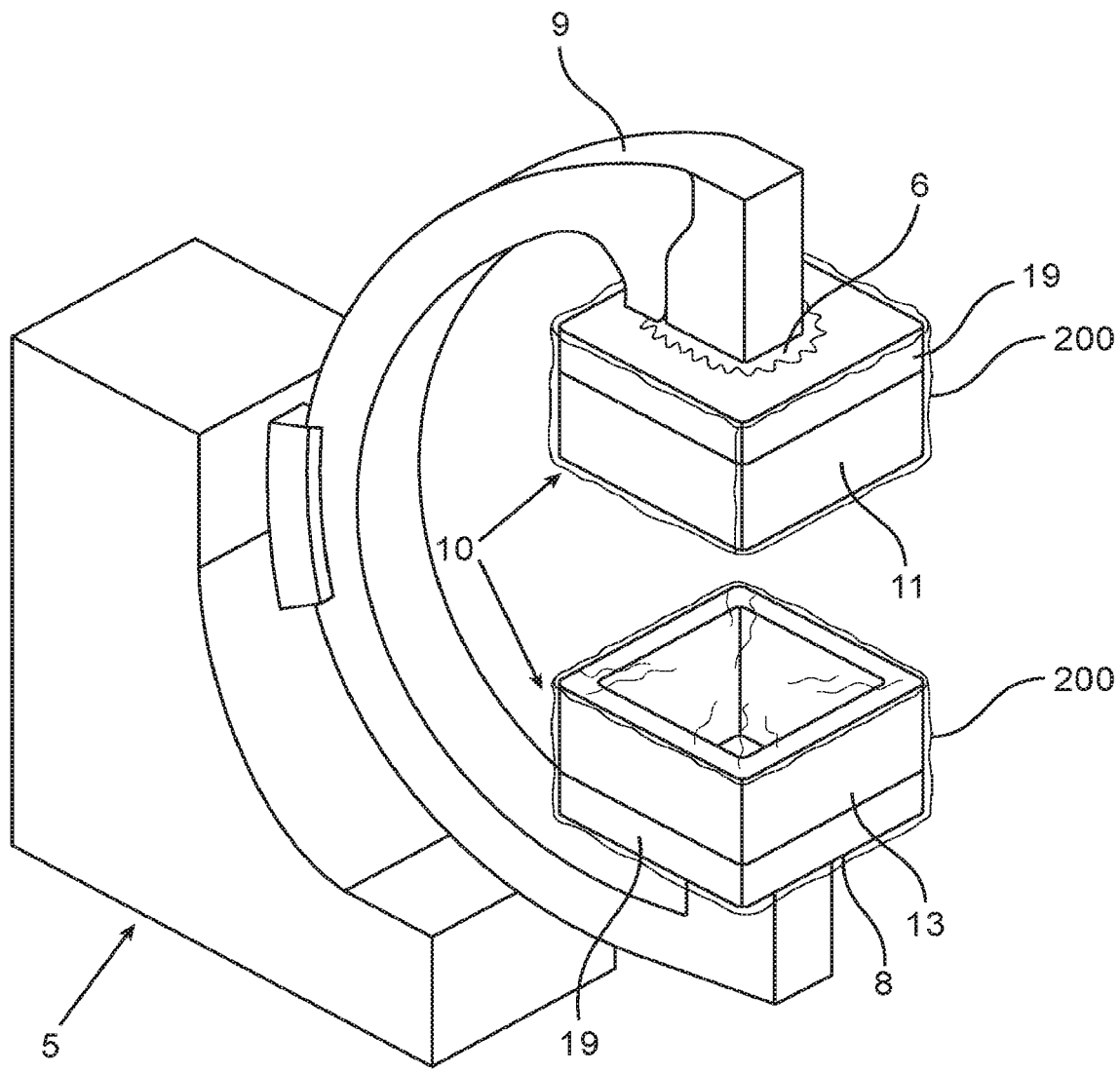

FIGS. 3A and 3B show an exemplary radiation shield cover 200 in the retracted and extended positions, respectively. As illustrated, cover 200 may be configured to completely cover radiation shields 11 and 13 to thereby provide a sterile barrier between the shields 11, 13 and the patient 1. Optionally, cover 200 also covers all or a portion of radiation detector 6 and/or radiation source 8. Alternatively, cover 200 may be shaped and sized to at least cover the areas which are in close proximity or which come into contact with the patient 1.

As radiation shields 11, 13 are configured to dynamically retract and extend, cover 200 advantageously can retract and extend and thereby adapt to the dynamic dimensions/positions of shields 11, 13 and more or less conform to the shape of the shields. As elaborated in greater detail below, cover 200 may include a deployment mechanism to facilitate contraction/folding thereof, independently from the extension and retraction motion mechanism of the shields 11 and 13. Alternatively, the cover may be folded/contracted along with the retraction of the shields 11, and 13. To avoid any resistance forces on shields 11, 13 and/or constraints to its extension mechanism, the cover may be extended passively, i.e., along with the extension of shields 11 and 13, optionally due to the extension forces the radiation shield applies on the cover. Alternatively, the cover may be actively extended.

Figure 4:
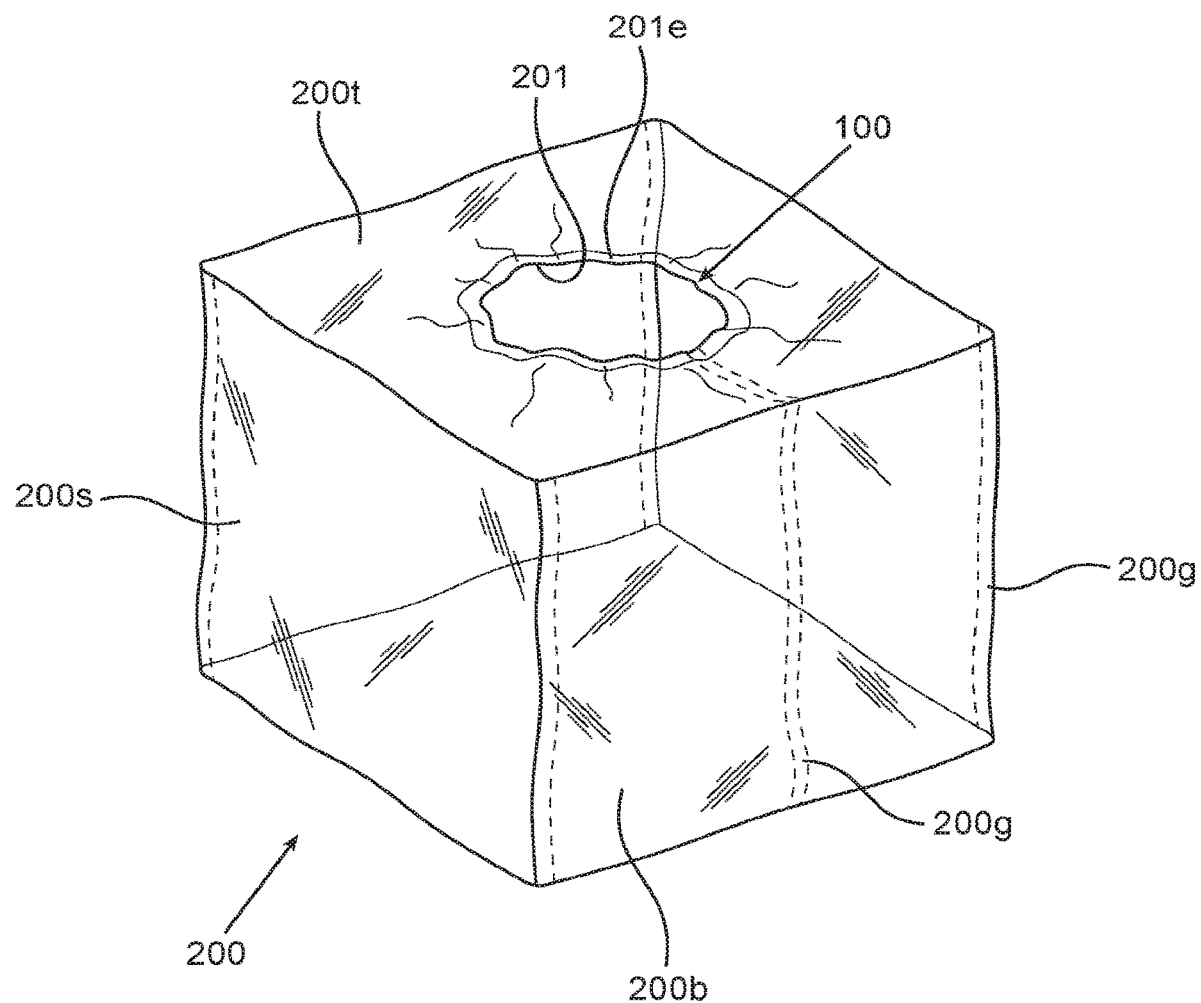
FIG. 4 is a perspective view of the radiation shield cover, in accordance with embodiments of the present invention.

FIG. 4 shows a design of shield cover 200 having four sides 200s; a bottom 200b; and a cover top 200t (where the terms "bottom" and "top" are in accordance with the orientation of the cover illustrated in FIG. 4, and can be in reverse orientation depending on whether the cover is covering upper radiation shield 11 or lower radiation shield 13). The illustrated four cover sides 200s form a square-like profile, nevertheless, rectangular-like or circular-like profiles are also contemplated. Cover top 200t includes a connection mechanism 100 for example an opening 201 with a peripheral elastic band 201e, as illustrated (for example, similar to a common shower cap) to facilitate connection to radiation detector 6 or radiation source 8, and/or support base 19 of radiation shielding apparatus 10. Optionally, cover top 200t can be attached via connection mechanism 100 in an alternative manner, such as by an adhesive strip, hook and loop fasteners, clips, hooks and so on.

In some designs, sides 200s are configured to attach to radiation detector 6 or radiation source 8, and/or support base 19 without the need for top 200t. In such a case, sides 200s may include connection mechanism 100 incorporating an adhesive strip, hook and loop fasteners, clips, hooks, rubber bands and so on.

Cover 200 may have one or more stitching 200g at the corner edges and/or along sides 200s for reinforcement. Cover 200 may be disposable, intended for one-time use or alternatively intended for repeated use after cleaning/sterilizing. Cover 200 can be designed to be low weight; and/or to be cost effective (e.g. be made of a low cost thin-sheet polymer). Advantageously, cover 200 may be manufactured of a material that can undergo a sterilization process via various techniques, such as by chemical sterilization, UV radiation, and the like.

Additionally, due to its material characteristics and design, cover 200 is particularly compact in size and/or shape when retracted (e.g. folded). In one or more embodiments, cover 200 is compactly foldable such that it is extendable to a length and/or volume of up to about 1000% of the collapsed/retracted size. For example, cover 200 may be extendable to a length and/or volume of up to about 900%, up to about 800%, up to about 700%, up to about 600%, up to about 500%, up to about 450%, up to about 400%, up to about 350%, up to about 300%, up to about 250%, up to about 200%, or up to about 150% of the collapsed size.

Prior art sterile covers of C-arm radiation shielding apparatus 10, which are static, i.e., non-deployable, may be considerably bigger and bulkier and more cumbersome. Shield cover 200 advantageously provides a sterile cover for X-ray systems, such as C-arm X-ray system 5, and can cover an entire radiation shielding unit (e.g., a shielding unit of the detector/source) and optionally dynamically extend and/or retract in accordance therewith, or along with, radiation shielding apparatus 10.

Sterile cover 200 may be transparent, translucent or opaque. Various materials for manufacturing the herein disclosed cover 200 are contemplated and may be applicable. Non-limiting examples of cover materials include polyethylene and polyvinyl chloride. Sterile cover 200 is designed so it can extend and/or retract according to the dynamic dimensions of the radiation shield 11, 13.

Figure 5:
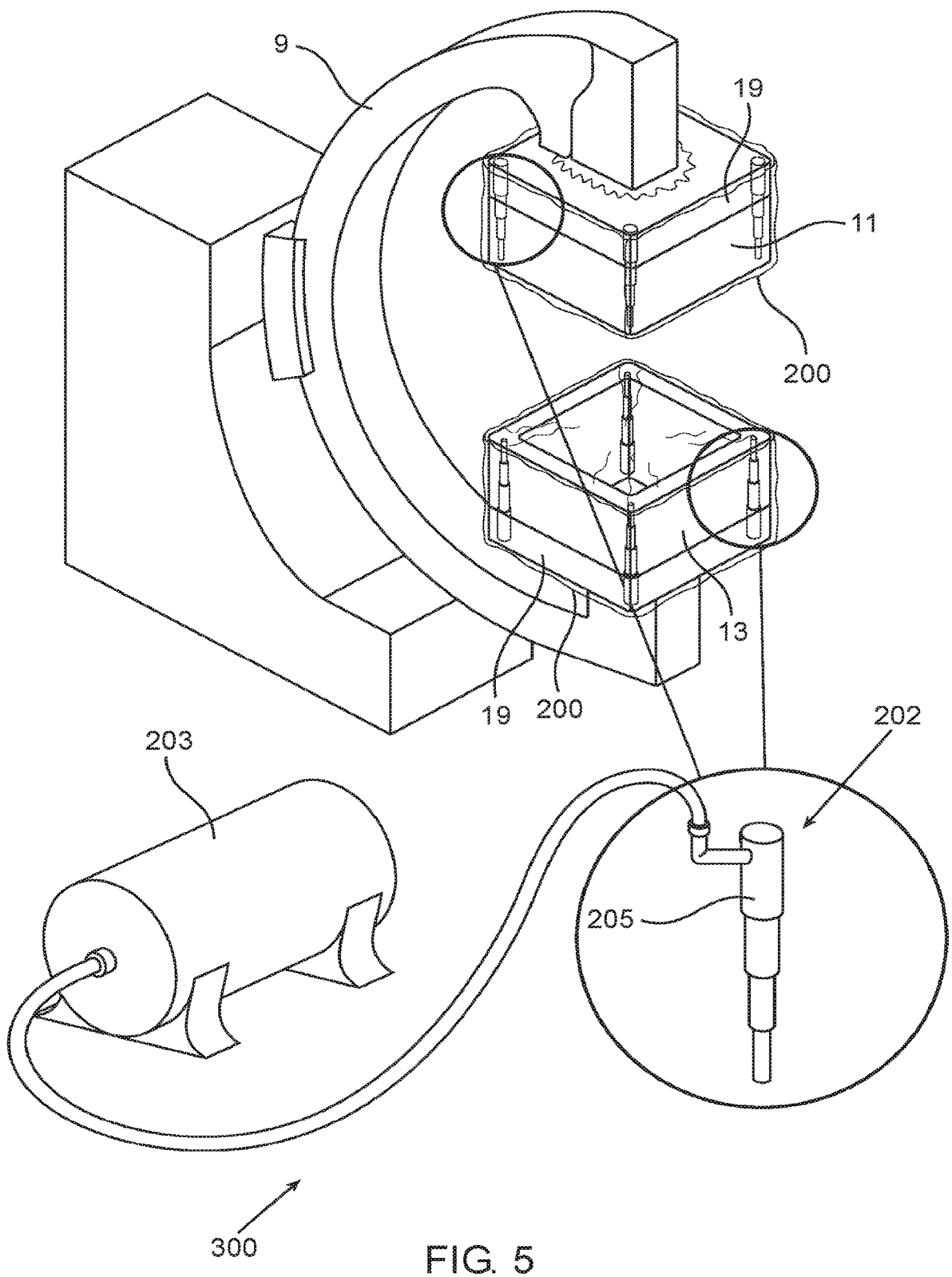
FIG. 5 is a perspective view of the radiation shield cover associated with an exemplary shield cover deployment mechanism therefor, including a hydraulic telescopic device, in accordance with embodiments of the present invention.

FIG. 5 illustrates a deployment mechanism 300 associated with radiation shield cover 200. To avoid any constraints on the dynamic properties of shields 11, 13, and particularly on the extension mechanism thereof, cover 200 may be configured to passively extend along with the extension of shields 11, 13. Nevertheless, deployment mechanism 300 may also facilitate extension of cover 200. Deployment mechanism 300 may be a hydraulic type and may include a pump 203 fluidly connected to a deployment device 202 in the form of at least one hydraulic telescopic device 205, for example including hydraulically operated segments or pistons. Extension of cover 200 via extension of hydraulic telescopic device 205 may be performed before or along with the extension of radiation shields 11 and 13; and retraction of the cover (retraction of hydraulic telescopic device 205) may be performed after or along with the retraction of the radiation shields.

Cover 200 can be extended/retracted when deployment device 202, in particular hydraulic telescopic device 205 thereof, is operated by pump 203. The hydraulic telescopic device 205 is preferably light weight and may be made of a polymeric material, such as PVC, polyethylene, an amide, PTFE, PET, PEEK or the like; or may be made of a light-weight metal, such as aluminum. Alternatively, or additionally, the pistons may be made of a light-weight rigid material such as a carbon fiber material. Hydraulic telescopic device 205 may be low cost and low weight.

Hydraulic telescopic device 205 may include plastic rings (not visible) serving as stoppers for each segment of the device and/or serve as gaskets to provide an effective fluid flow by pump 203. Advantageously, the retraction and/or extension is conducted by flowing one or more liquids via hydraulic telescopic device 205 and there is no particular requirement of providing an "air-tight" seal for the required retraction/extension function. Using a low volume hydraulic telescopic device 205 (e.g., 20-50 cc), a pneumatic flow of about 100-300 cc per second at low pressure may be sufficient for the deployment. Alternatively, hydraulic telescopic device 205 can be retracted and/or extended with air pressure while at least one of the retraction/extension operations can be achieved passively without air pressure, i.e., via gravity and/or operation (extension/retraction) of the radiation shield 11, 13. Optionally, pump 203 activates retraction of cover 200 by applying negative air pressure, which actively contracts the hydraulic telescopic device 205 to arrange the cover in a retracted position, e.g. folded or crinkled.

Deployment device 202 can be designed to effect only the retraction of cover 220. Deployment device 202 can be designed to effect only the extension of cover 220. Optionally, deployment device 202 can be designed to effect both the extension and retraction of cover 220. Optionally, deployment device 202 can be disposed in at least one corner of cover 200. Optionally, deployment device 202 can be disposed in at least one face corner of cover 200. Deployment device 202 includes means to directly or indirectly connect it or a portion or a unit thereof to support base 19 and/or radiation shields 11 and 13.

In one or more embodiments, sterile cover 200 is operatively deployable along with the movement (i.e. extension and retraction) of shields 11, 13 during the X-ray procedure.

Further exemplary deployment devices 202 for the extension and/or retraction of cover 200 include at least one pneumatic piston; hydraulic piston; telescopic piston; elastic band; cable, wire; spring; electric piston; hook and loop fastener; mechanical piston; anchoring point; and any combination thereof. Deployment device 202 may be attached at various positions of cover 200. For example, deployment device 202 may be attached to a distal end of cover 200 and/or to any point along the length of shield 11, 13.

In one or more embodiments, cover 200 effectively covers or seals radiation shield 11, 13; or a portion thereof, typically covering at least free edges 17. Cover 200 may be adjusted or modified to the contour/length/width of one or more dimensions of radiation shielding apparatus 10 or a portion thereof. Cover 200 may include a mechanism to directly or indirectly connect the cover, or a portion thereof, or a unit thereof, to the radiation shielding apparatus 10 and/or to the X-ray imaging system 5. Optionally, cover 200 covers about 50% or more of each radiation shield 11, 13.

Figure 6A:
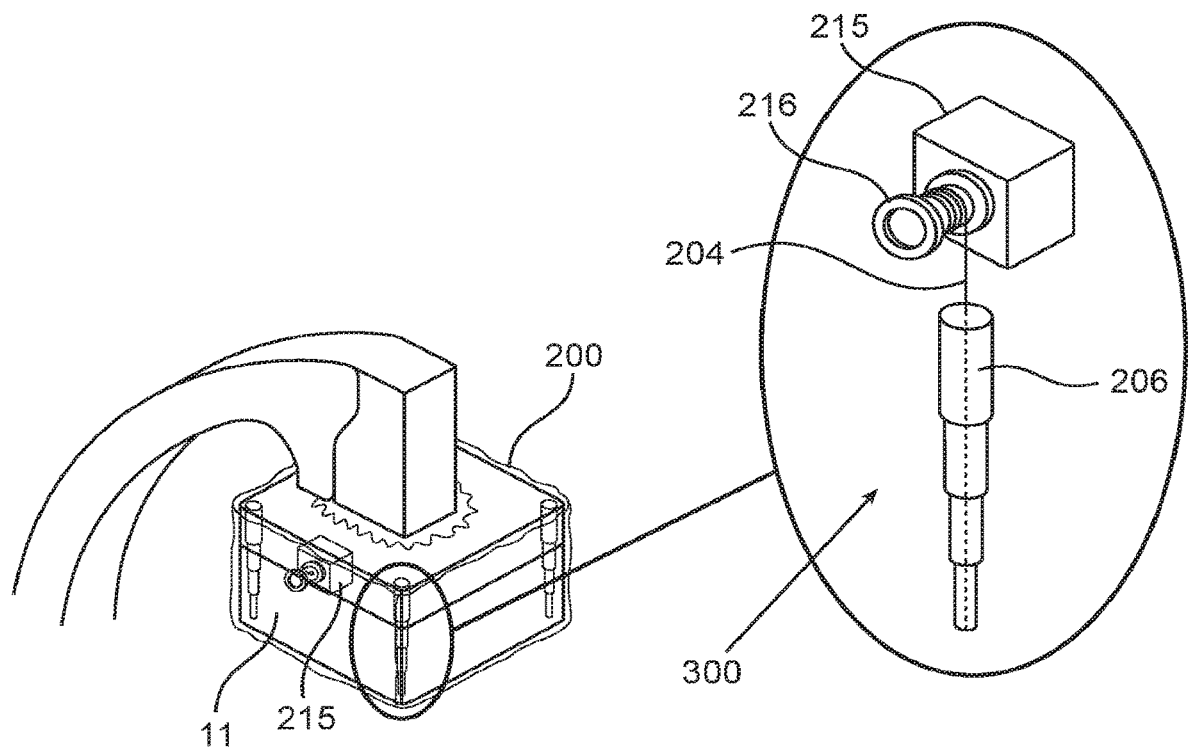
FIGS. 6A and 6B are perspective views of the radiation shield cover, respectively attached to the detector and the radiation source of the C-arm and illustrating another exemplary shield cover deployment mechanism including a motor with a spool-like motor shaft, in accordance with embodiments of the present invention.
Figure 6B:
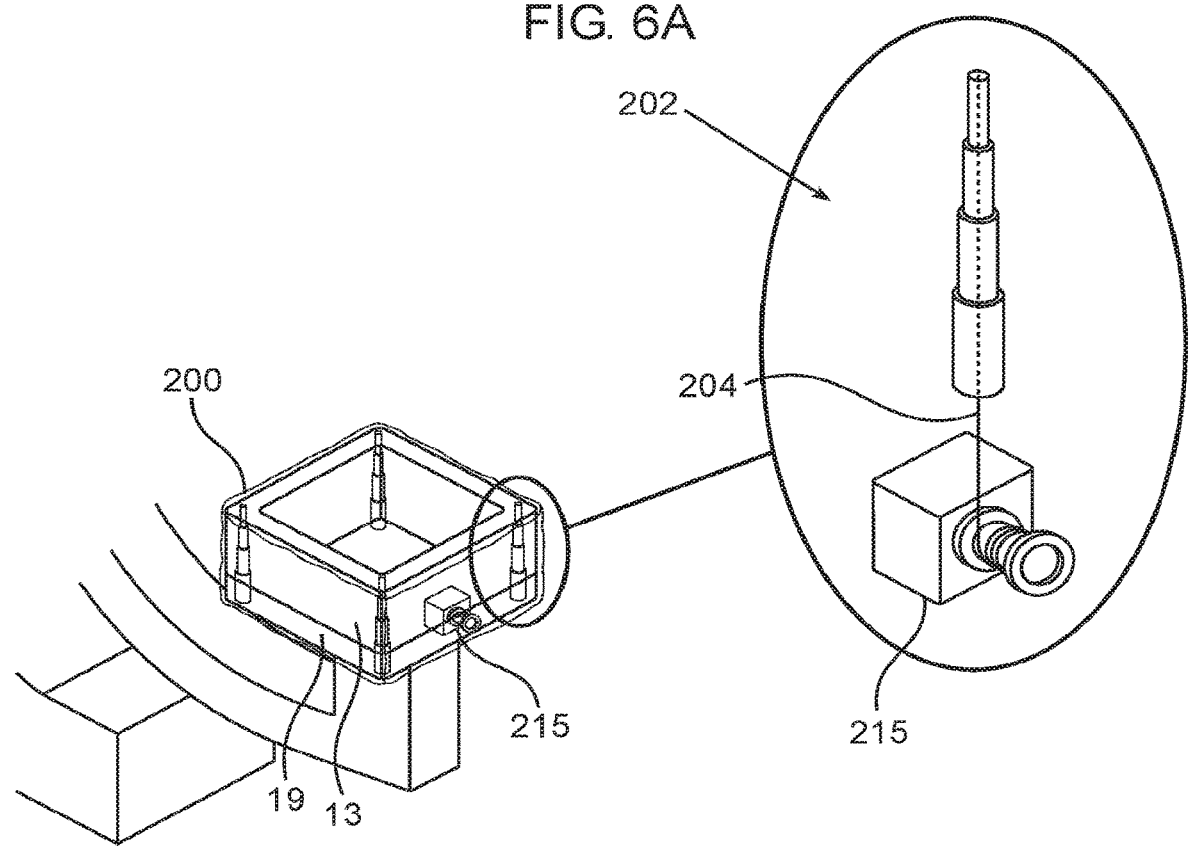

FIGS. 6A and 6B respectively illustrate upper and lower radiation shield covers 200 and deployment mechanism 300, wherein the mechanism includes a deployment device 202 including a motor 215 with a spool-like motor shaft 216; and a cable 204 connecting the motor shaft 216 to a mechanical telescopic device 206, which is connected, in particular at its distal end, to cover 200. Motor 215 can be activated to spin motor shaft 216 in either direction so as to wind or unwind cable 204 so as to extend or retract mechanical telescopic device 206, thereby extending or retracting cover 200.

Mechanical telescopic device 206 may include one or more springs (not shown) to bias the device in an extended position. Thus, motor 215 winding up cable(s) 204 on motor shaft 216 can cause mechanical telescopic device 206 to be moved against the bias of the spring to retract cover 200, which can be independent and/or along with the retraction of radiation shield 11, 13.

Figure 7:
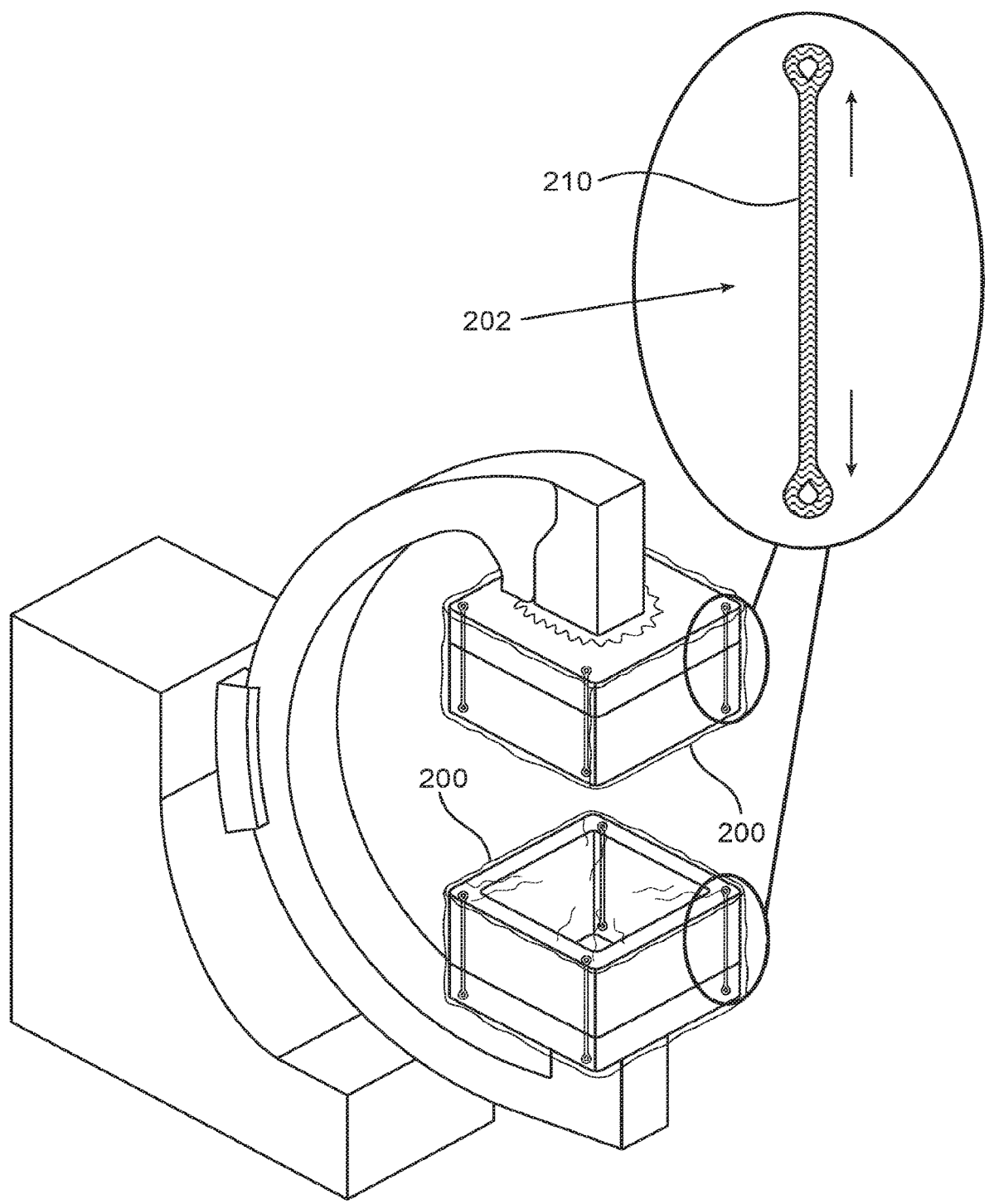
FIG. 7 is a perspective view of another exemplary shield cover and exemplary deployment mechanism therefor, including elastic bands, according to embodiments of the invention.

FIG. 7 illustrates yet another exemplary deployment device 202 including at least one elastic band 210 made of an elastic material. Elastic bands 210 may be connected to the sterile cover 200 via at least one strip of stitches (not visible), or by adherence/connection by any suitable technique. Elastic bands 210, and optionally also cover 200, are connected to radiation shield 11, 13 such that when the radiation shielding apparatus 10 is extended, the cover is extended along with shielding apparatus 10. Elastic bands 210 are configured to apply a resisting force on cover 200 when extended. Due to the elastic-pulling force of elastic bands 210, cover 200 will fold/retract when radiation shield 11, 13 retract.

Figure 8:
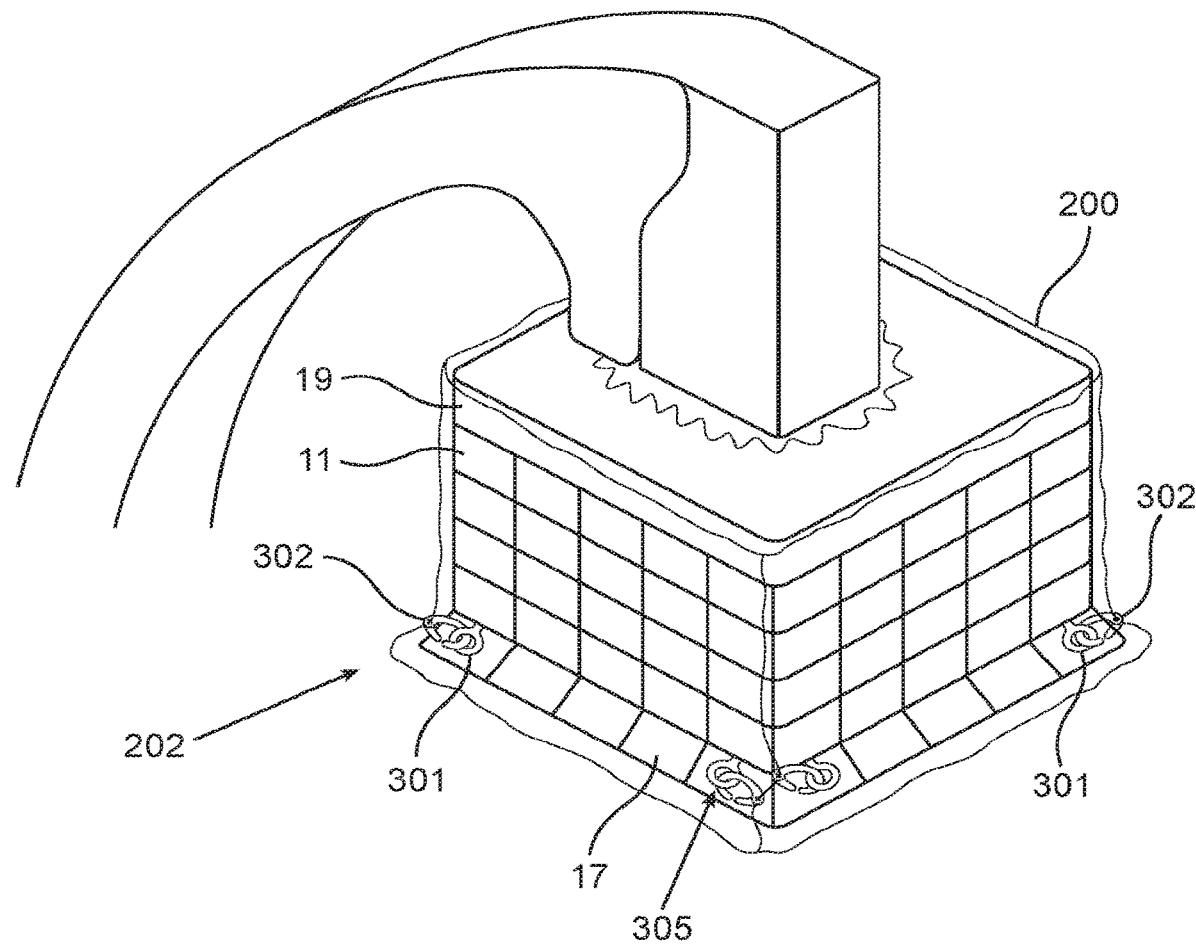
FIG. 8 is a perspective view of yet another exemplary shield cover and exemplary deployment mechanism therefor, including cover-to-shield fasteners, according to embodiments of the invention.

FIG. 8 depicts yet another exemplary deployment device 202, which includes at least one cover-to-shield fastener 305, each fastener exemplified by an anchor 301, connected close to free edges 17 of shield 11, 13 at the external side thereof; and a hook 302 connected to a point close to the distal end of the internal side of cover 200. As a result of the connection of anchor 301 and hook 302, cover 200 will move along with the movement (extension and retraction) of shield 11, 13. Various alternative cover-to-shield fasteners for connecting between cover 200 and radiation shield 11, 13 are contemplated, including hook-and-loop fasteners; clips; snaps; adhesive; and the like.

Figure 9A:
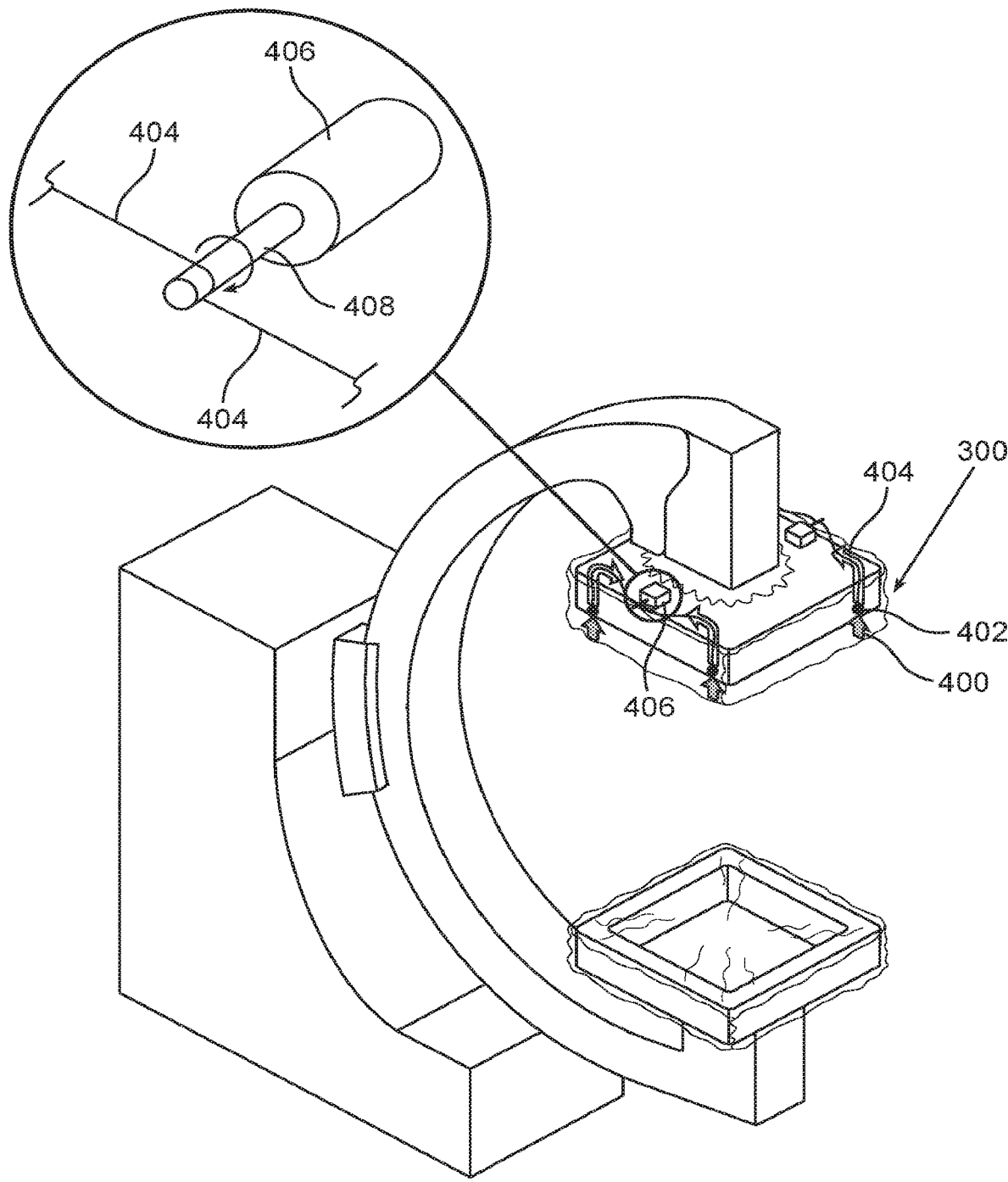
FIGS. 9A and 9B are schematic perspective views of the radiation shield cover, respectively in the retracted and extended positions, illustrating exemplary details of the shield cover deployment mechanism, in accordance with embodiments of the present invention.
Figure 9B:
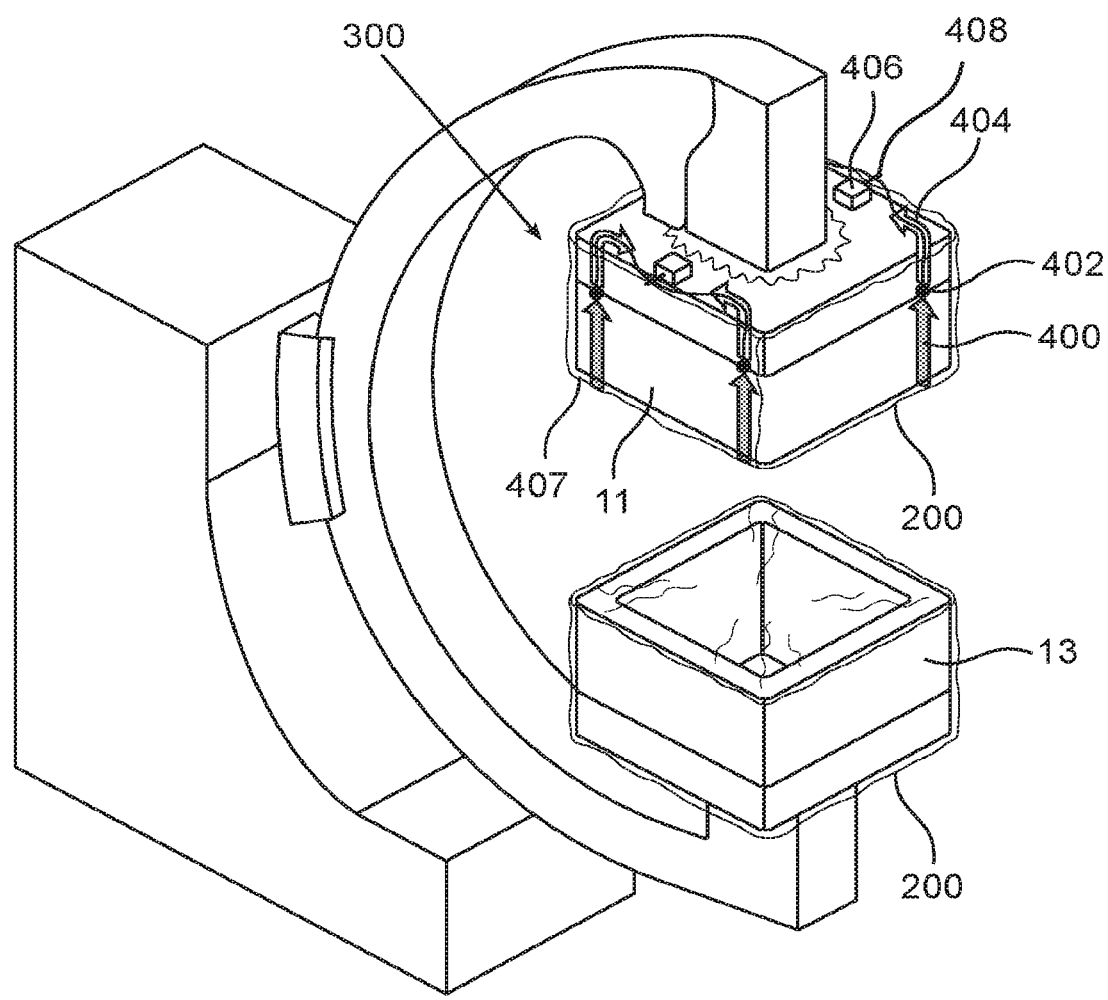

FIGS. 9A and 9B show another exemplary deployment mechanism 300 in the retracted and extended positions, respectively. In this design, deployment mechanism 300 includes at least one shield cover cable 400; at least one inter-cable fastener 402; at least one motor-shaft cable 404; and at least one electric motor 406 having a motor shaft 408. Shield cover cable 400 is connected at one end to a distal portion 407 of cover 200 and at the other end to inter-cable fastener 402. Motor-shaft cable 404 is connected at one end to inter-cable fastener 402 and at the other end to motor shaft 408.

Mechanism 300 may include one motor 406, two motors 406, three motors 406 or four motors 406, each disposed within or adjacent support base 19, and/or upper portions of shields 11 and 13, and/or radiation adjacent radiation source 6, and/or radiation detector 6.

As illustrated, motor 406 may be connected to two motor-shaft cables 404 disposed along one face of cover 200, where one of the shaft cables is attached at a lower portion/side of motor shaft 408 and another shaft cable is attached at an upper portion/side of motor shaft 408. As such, when motor 406 is operated and motor shaft 408 rotates, both cables 404 will simultaneously be wound on the shaft, or simultaneously unwind from the shaft.

To allow cover 200 to extend with the shield 11, 13, motor 406 is set in a motor-shaft disengagement mode whereby shaft 408 can freely rotate to allow the cover to extend via (along with) the movement (extension) of the shields 11 and 13. During retraction of cover 200, shaft 408 is set in a motor-shaft engagement mode whereby when shaft 408 rotates the cover will retract.

Being connected to cover 200, shield cover cable 400 may be configured to be removed or replaced along with cover 200, while motor-shaft cable 404 may be permanently attached to motor 406. Alternatively, both shield cover cable 400 and motor-shaft cable 404 are replaceable and can be removed from any attachment with cover 200 and/or radiation shield 11, 13 and/or support base 19. Alternatively, both shield cover cable 400 and motor-shaft cable 404 are permanent. Optionally, either one or both motor-shaft cable 404 and shield cover cable 400 is made of a radiolucent material, such as composite materials including radiation attenuating materials and carbon fibers. Alternative materials may include plastic cables made of moldable polymers, such as polyamides, etc.

Figure 10:
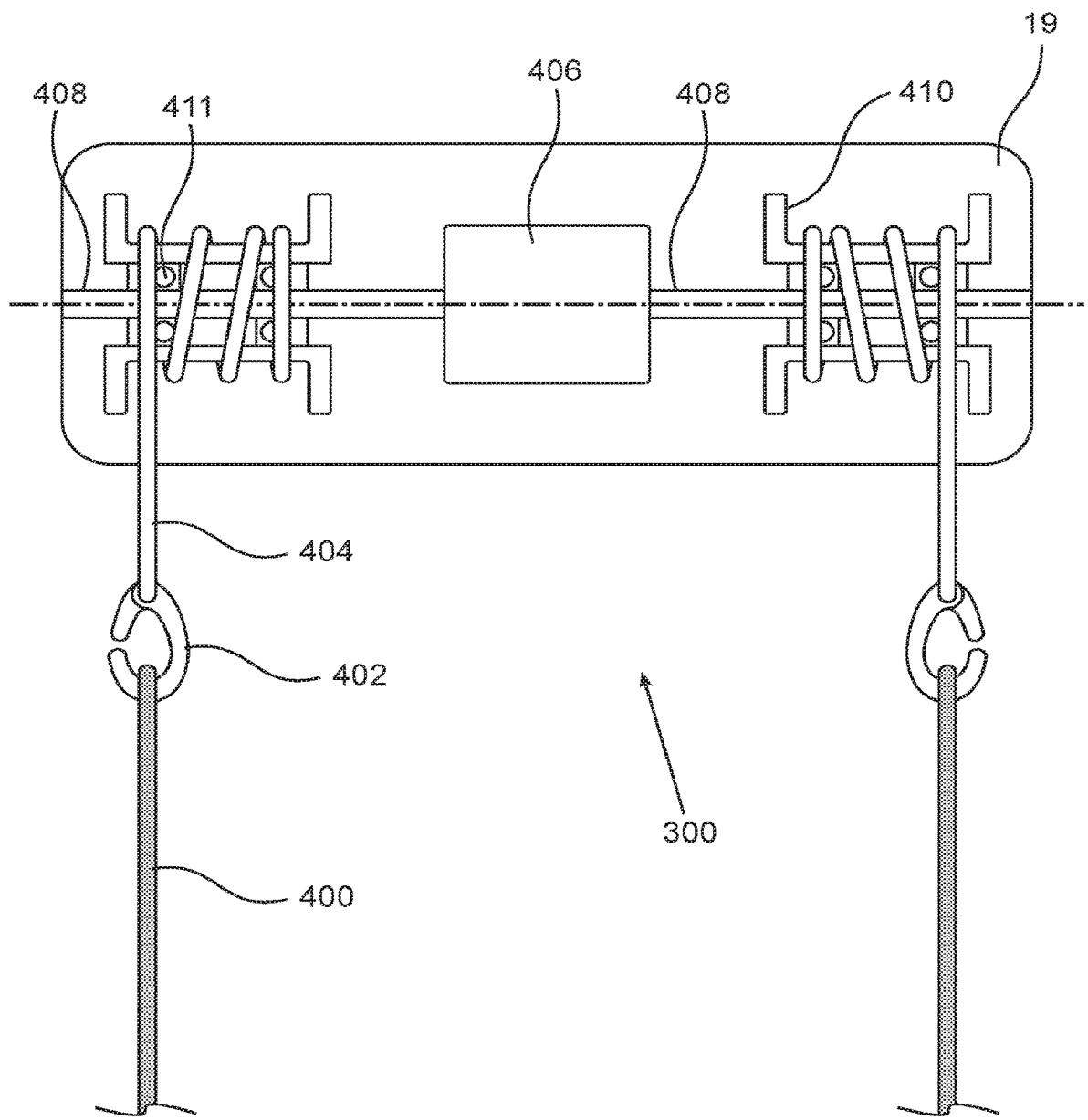
FIG. 10 is a schematic side view illustrating another exemplary shield cover deployment mechanism including a spinning motor, in accordance with embodiments of the present invention.

FIG. 10 illustrates an alternative motor 406 with oppositely extending motor shafts 408. Each shaft 408 may have a shaft accessory 410 disposed on the shaft and equipped with one or more bearing element 411. The shaft accessory 410 may have a larger diameter than the shaft and be configured to have motor-shaft cable 404 simultaneously wind thereon during retraction of cover 200 and unwind therefrom during extension of the cover. Optionally, the force that shields 11, 13 apply on cover 200 during extension thereof is higher than the friction force applied on the bearing element 411, motor 406, and/or motor shaft 408, thereby allowing passive extension of cover 200 when the shields 11, 13 extend. Further optionally, when shields 11, 13 extend, motor 406 may be set in a released or free mode whereby cables 400 and 404 can move in the direction of the shield (downward in FIG. 11) and cover 200 can freely move with the shields 11, 13.

Figure 11:
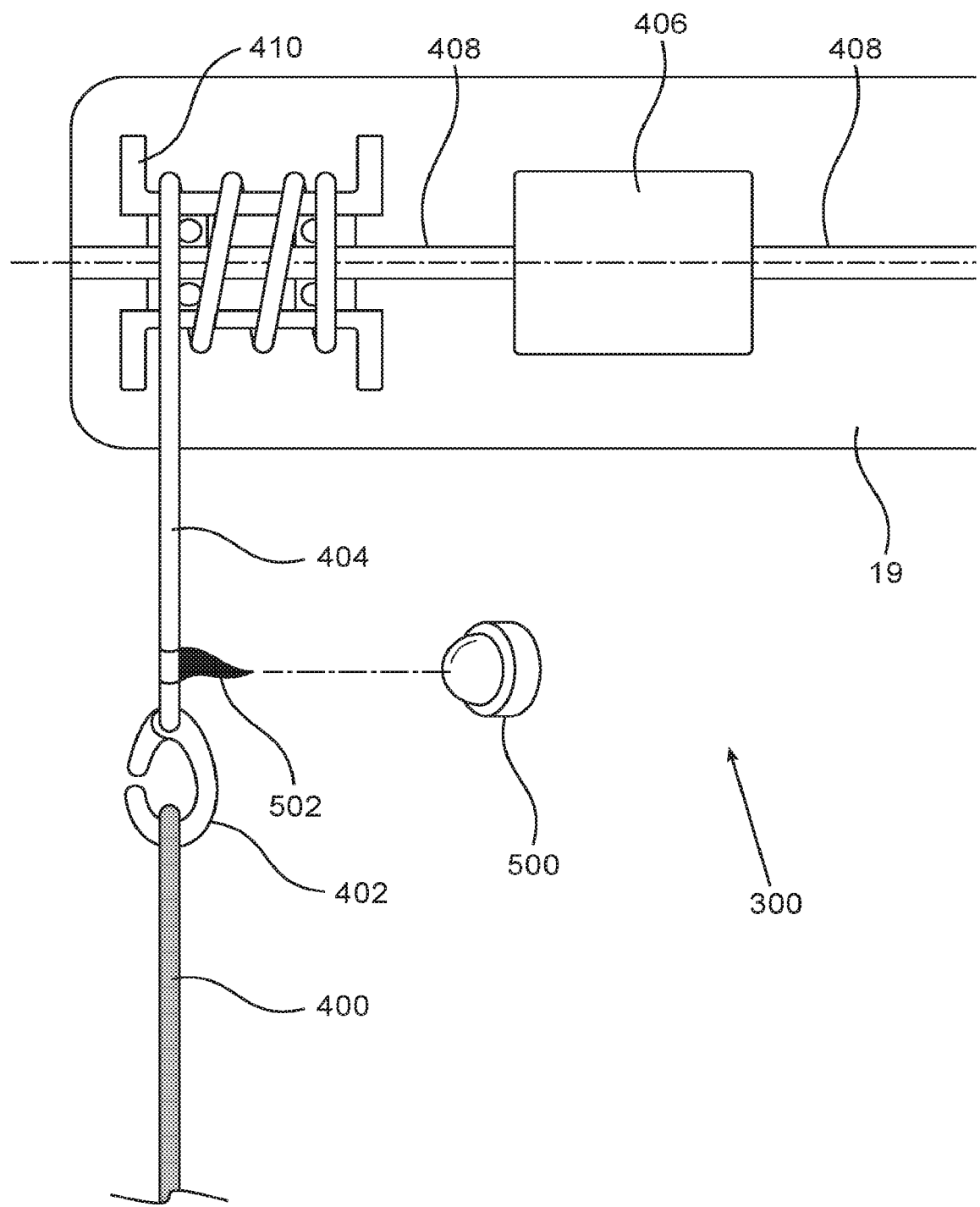
FIG. 11 is a schematic side view of yet another exemplary shield cover deployment mechanism including a motor-stop sensor, according to embodiments of the invention.

FIG. 11 illustrates an alternative design to that of FIG. 10 wherein deployment mechanism 300 includes a motor-stop sensor 500 and a visual sensor stop flag 502. In operation, motor-stop sensor 500 senses when flag 502 arrives in the retracting direction (upward in FIG. 11) and sends a signal to motor 406 to stop operating and thereby prevent overwind. Although stop flag 502 is illustrated as attached to motor-shaft cable 404, the stop flag may be alternatively coupled to cover cable 400. Optionally, when shields 11, 13 extend, motor 406 may be set in a released or free mode whereby cables 400 and 404 can move in the direction of the shield (downward in FIG. 11) and cover 200 can freely move with the shields 11, 13.

Figure 12:
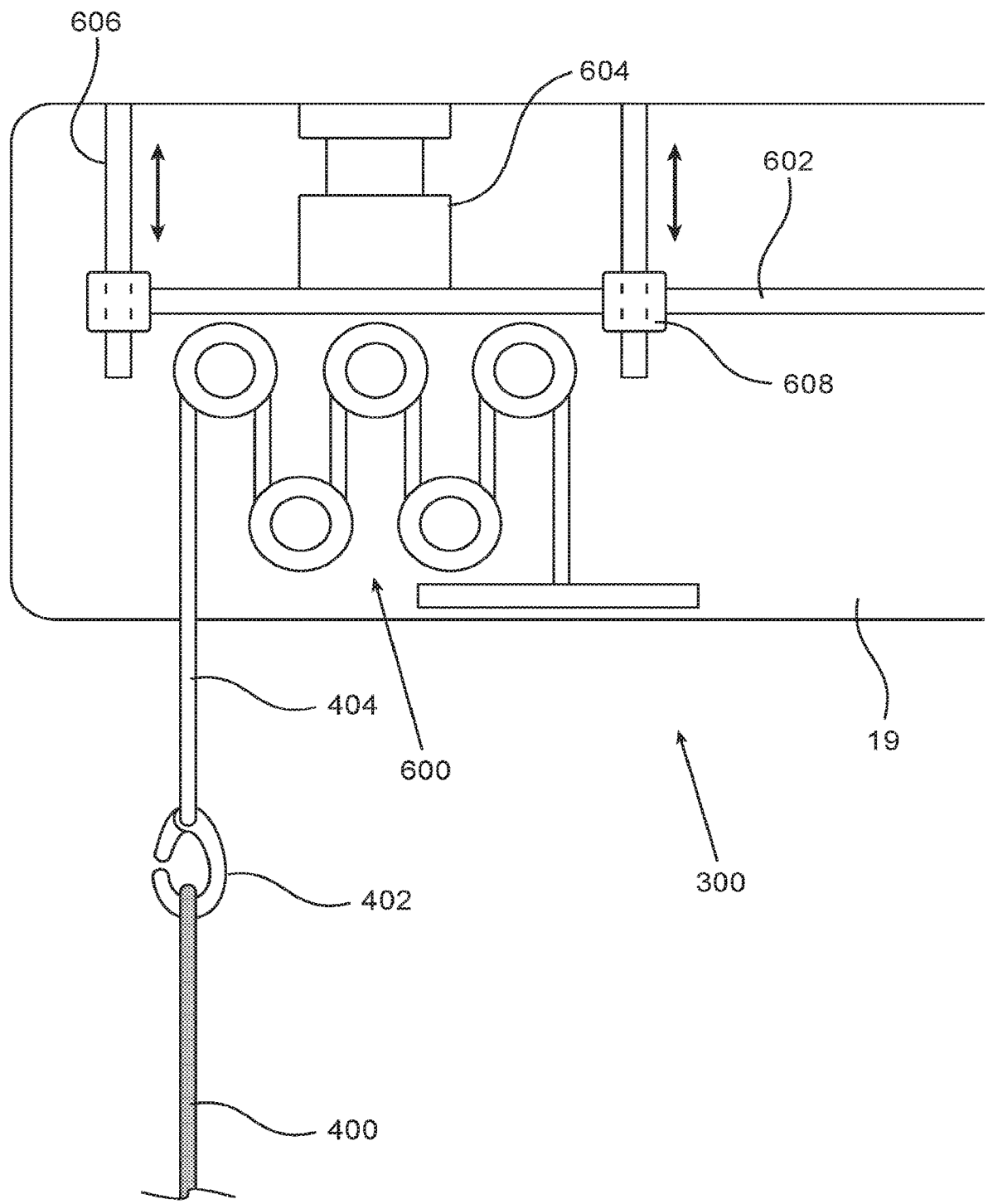
FIG. 12 is a schematic side view of yet another exemplary shield cover deployment mechanism including a pulley system, according to embodiments of the invention.

FIG. 12 shows another alternative design of deployment mechanism 300 wherein release of, and pulling on, shield cover cable 400 and motor-shaft cable 404 is accomplished by a pulley system 600 that is configured to contract and expand to respectively release and pull the cables 400, 404. Attached to pulley system 600 is a generally horizontal rod 602, which is raised and lowered by a linear motor 604. The up and down movement of rod 602 may be stabilized by one or more vertical stabilizing rods 606 upon which one or more stabilizing rings 608 can slide.

When shields 11, 13 extend, linear motor 604 may be set in a released or free mode whereby rod 602 can move in the direction of the shield (downward in FIG. 12) and cover 200 can freely move with the shield. To retract cover 200, linear motor 604 is set in an active mode to pull on rod 602 to in turn pull cables 400 and 404 in a retracting direction.

Figure 13A:
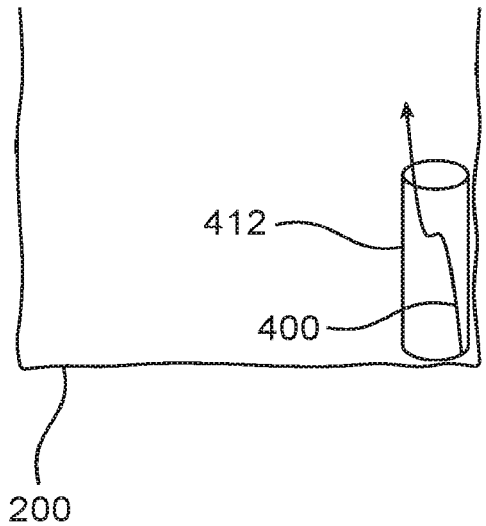
FIGS. 13A-13D are schematic side views illustrating additional exemplary options of the shield cover deployment mechanism, in accordance with embodiments of the present invention.
Figure 13B:
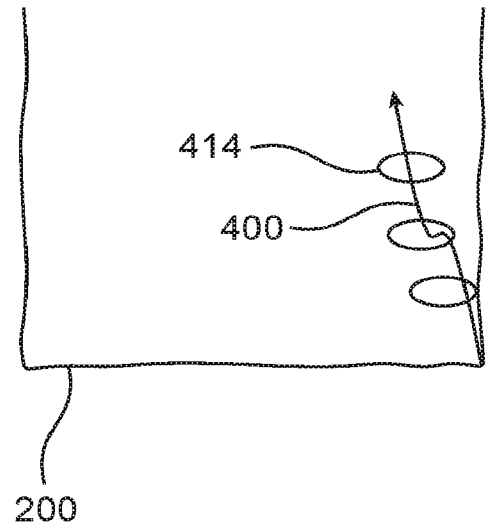

FIGS. 13A-13D illustrate further designs of deployment mechanism 300 exemplifying options for attaching shield cover cable 400 to cover 200. FIG. 13A shows an option where shield cover cable 400 is attached to a corner of cover 200 and the shield cover cable 400 runs through a cylinder or sleeve 412. FIG. 13B shows a similar design to that of FIG. 13A, however instead of sleeve 412, shield cover cable 400 runs through a series of rings 414.

Figure 13C:
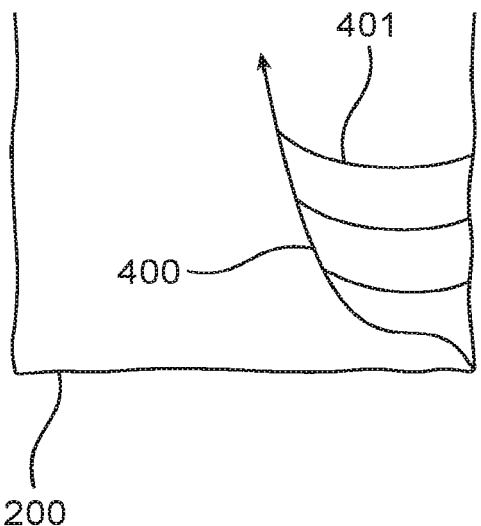
Figure 13D:
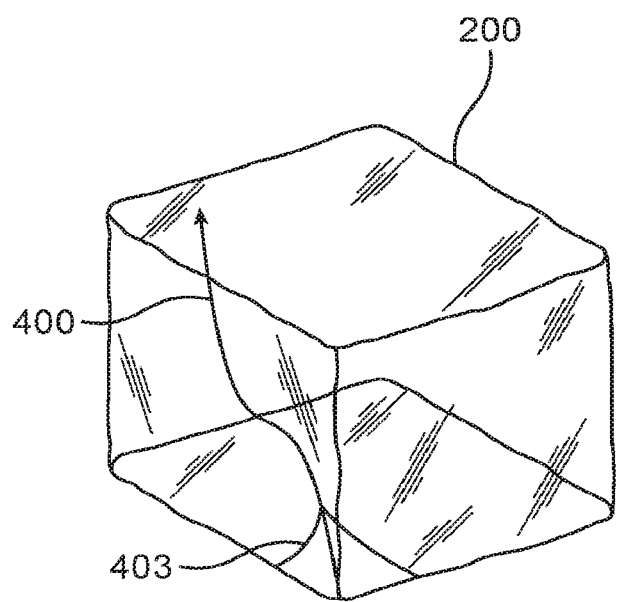

In FIG. 13C, shield cover cable 400 has a series of cable-to-cover cables 401 extending from a series of locations along the shield cover cable 400 to a series of corresponding locations along an edge of cover 200. In FIG. 13D, shield cover cable 400 has a plurality of cable-to-cover cables 403 extending from the distal end of shield cover cable 400 to locations including those at and adjacent a corner of cover 200.

Each of the terms: 'includes', 'including', 'has', 'having', 'comprises', and 'comprising', and their derivatives, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof.

The term 'consisting essentially of' means that the scope of the claim is limited to the specified elements and those that do not materially affect the basic and novel characteristic(s) of the claimed device and materials.

The phrases 'consisting of' and 'consists of', and their derivatives, as used herein, means 'including and limited to'.

The term 'method', as used herein, refers to steps, procedures, manners, means, and/or techniques, for accomplishing a given task including, but not limited to, those steps, procedures, manners, means, and/or techniques, either known to, or readily developed from known steps, procedures, manners, means, and/or techniques, by practitioners in the relevant field(s) of the disclosed invention.

Throughout this disclosure, a numerical value of a parameter, feature, characteristic, object, or dimension, may be stated or described by a numerical range. Such a numerical range, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', and derivatives thereof, is considered equivalent to, and meaning the same as, the phrase 'in a range of from about a first numerical value to about a second numerical value', and, thus, the two equivalently meaning phrases may be used interchangeably.

The term 'about', in some embodiments, refers to ±30% of the stated numerical value. In other embodiments, the term refers to ±20% of the stated numerical value. In yet other embodiments, the term refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub combination in the context or format of a single embodiment, may also be illustratively described and presented in the context or format of a plurality of separate embodiments.

Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

All publications, patents, and patent applications mentioned in this specification are herein incorporated in their entirety by reference into the specification, to the same extent as if each individual publication, patent or patent application was specifically and individually recited herein. In addition, citation or identification of any reference in this application shall not be construed as an admission that such reference is considered as prior art to the present invention. To the extent that section headings are used, they should not be construed as necessarily limiting.

It should be understood that the above description is merely exemplary and that various embodiments of the present invention that may be devised, mutatis mutandis, and that the features described in the above-described embodiments, and those not described herein, may be used separately or in any suitable combination; and the invention can be devised in accordance with embodiments not necessarily described above.

What is claimed is:

1. A radiation shield cover for covering a radiation shield of an X-ray system, the cover comprising:
   cover sides;
   a cover bottom at the bottom of the cover sides configured to prevent contact of the radiation shield with a patient;
   a connection mechanism for connecting the cover to a radiation detector and/or a radiation source, and/or the radiation shield of the X-ray system; and
   a deployment mechanism comprising a motor configured to retract and/or extend the shield cover when the radiation shield retracts and/or extends, or thereafter.

2. The cover of claim 1, wherein the cover sides are configured to attach to the radiation detector and/or the radiation source and/or the radiation shield.

3. The cover of claim 1, wherein the connection mechanism includes a cover top with an opening having a peripheral elastic band.

4. The cover of claim 1, wherein the cover is designed to be disposable.

5. The cover of claim 1, wherein the deployment mechanism is configured to retract the radiation shield cover.

6. The cover of claim 1, wherein the deployment mechanism comprises a pump fluidly connected to at least one hydraulically operated telescopic device, which is operably connected to the cover, wherein the pump is driven by the motor.

7. The cover of claim 1, wherein the deployment mechanism comprises a cable operably connected to the motor and a telescopic device.

8. The cover of claim 1, wherein the motor comprises at least one electric motor having a shaft and the deployment mechanism comprises at least one shield cover cable; at least one inter-cable fastener; at least one motor-shaft cable; wherein the shield cover cable is connected at one end to a distal portion of the cover and at its other end to inter-cable fastener, and motor-shaft cable is connected at one end to inter-cable fastener and at its other end to the motor shaft, wherein during retraction of the cover, the motor-shaft cable is configured to wound on the motor shaft and wherein during extension, the motor-shaft cable is configured to unwind on the motor shaft.

9. The cover of claim 8, wherein the at least one electric motor is connected to two motor-shaft cables disposed along a same face of the cover, where one of the shaft cables is attached at a lower portion or side of the motor shaft and the other motor-shaft cable is attached at an upper portion or side of the motor shaft, whereby when the electric motor is operated and motor shaft rotates, the two motor-shaft cables are simultaneously wound on the motor shaft or simultaneously unwind from the shaft.

10. The cover of claim 8, wherein the at least one motor shaft has a shaft accessory with a shaft bearing disposed thereon, the shaft accessory having a larger diameter than the shaft and being configured with a motor-shaft cable to simultaneously wind on the shaft during retraction of the cover and to unwind therefrom during extension of the cover.

11. The cover of claim 8, wherein the motor-shaft cable and/or the shield cover cable comprises a motor-stop sensor and a visual sensor stop flag, the motor-stop sensor configured to sense when flag arrives in the retracting direction and to send a signal to the electric motor to stop operating and thereby prevent overwind.

12. The cover of claim 8, wherein the deployment mechanism comprises at least one pulley system configured to contract and expand to respectively release and pull the cables.

13. The cover of claim 12, wherein the at least one pulley system comprises a generally horizontal rod, which is raised and lowered by a linear motor.

14. The cover of claim 12, wherein the at least one pulley system further comprises one or more vertical stabilizing rods to stabilize the generally horizontal rod.

15. The cover of claim 13, wherein the horizontal rod, is stabilized by one or more vertical stabilizing rods upon which one or more stabilizing rings can slide.

16. The cover of claim 1, wherein the deployment mechanism comprises a shield cover cable attached to a corner of the cover and the shield cover cable runs through a sleeve.

17. The cover of claim 1, wherein the deployment mechanism comprises a shield cover cable attached to a corner of the cover and the shield cover cable runs through a series of rings.

18. The cover of claim 1, wherein the deployment mechanism comprises a shield cover cable with a series of cable-to-cover cables extending from a series of locations along the shield cover cable to a series of corresponding locations along an edge of the cover.

19. The cover of claim 18, wherein the cable-to-cover cables extend from the distal end of the shield cover cable to locations including those at and adjacent a corner at the bottom and one of the sides of the cover.

20. The cover of claim 1, wherein there are four cover sides forming a square-like profile.

* * * * *